United States Patent [19]
Ryland et al.

[11] Patent Number: 5,665,869
[45] Date of Patent: Sep. 9, 1997

[54] METHOD FOR THE RAPID REMOVAL OF PROTOPORPHYRIN FROM PROTOPORPHYRIN IX-CONTAINING SOLUTIONS OF HEMOGLOBIN

[75] Inventors: James R. Ryland, Louisville; Maura-Ann H. Matthews, Boulder; Ulrich P. Ernst, Lafayette, all of Colo.; Daniel E. Houk, Concord, Calif.; David W. Traylor, Wheat Ridge, Colo.; Lee R. Williams, Concord, Calif.

[73] Assignee: Somatogen, Inc., Boulder, Colo.

[21] Appl. No.: 153,071

[22] Filed: Nov. 15, 1993

[51] Int. Cl.$^6$ .................. C07K 14/805; A23J 1/00
[52] U.S. Cl. ............................ 530/412; 530/385
[58] Field of Search ........................ 530/350, 380, 530/385, 412, 423, 400

[56] References Cited

U.S. PATENT DOCUMENTS

| | | | |
|---|---|---|---|
| 4,301,144 | 11/1981 | Iwashita et al. | 424/78 |
| 4,321,259 | 3/1982 | Nicolau et al. | 424/101 |
| 4,336,248 | 6/1982 | Bonhard | 424/101 |
| 4,377,512 | 3/1983 | Ajisaka et al. | 260/112 |
| 4,473,563 | 9/1984 | Nicolau et al. | 424/224 |
| 4,598,064 | 7/1986 | Walder | 514/6 |
| 4,670,417 | 6/1987 | Iwasaki et al. | 514/6 |
| 4,831,012 | 5/1989 | Estep | 514/6 |
| 4,861,867 | 8/1989 | Estep | 530/385 |
| 4,975,246 | 12/1990 | Charm | 422/21 |
| 5,028,588 | 7/1991 | Hoffman et al. | 514/6 |
| 5,084,558 | 1/1992 | Rausch | 530/395 |
| 5,173,426 | 12/1992 | Fischer et al. | 435/252.3 |

FOREIGN PATENT DOCUMENTS

| | | |
|---|---|---|
| 0277289 | 11/1987 | European Pat. Off. |
| 8809179 | 5/1988 | WIPO |
| 9013645 | 5/1990 | WIPO |
| 9116349 | 4/1991 | WIPO |
| 9308831 | 10/1991 | WIPO |
| 9211283 | 12/1991 | WIPO |
| 9222646 | 6/1992 | WIPO |
| 9308842 | 11/1992 | WIPO |

OTHER PUBLICATIONS

Alves et al. (Oct 1993) Int. J. Biol. Macromol 15(5):273–279.

Antonini, E. & Brunori, M./Hemoglobin and Myoglobin in Their Reactions with Ligands/Frontiers of Biology/(1971), 21, Entire Text/North–Holland Publishing Co/Amsterdam.

Fermi, G. & Perutz, M.F./Atlas of Molecular Structures in Biology/2. Haemoglobin and Myoglobin/(1981)/Clarendon Press/Oxford/Entire Text.

Bunn, H.F. & Forget, B.G./Hemoglobin: Molecular, Genetic and Clinical Aspects/W.B. Saunders Co/Philadelphia/(1986)/Editor–John Dyson/Entire Text.

Beguin, P. et al./Identification of the Endoglucanase Encoded by the celB Gene of Clostridium Thermocellum/Biochimie/(1983)/65, 495–500.

Liebhaber, S.A. et al./Cloning and Complete Nucleotide Sequence of Human 5'–α–Globin Gene/PNAS/(1980)/77(12), 7054–7058.

Kunkel, T.A. et al/Rapid and Efficient Site–Specific Mutagenesis Without Phenotypic Selection/Methods in Enzymology/(1987)/154, 367–382.

Zoller, M.J. & Smith, M./Oligonucleotide–Directed Mutagenesis of DNA Fragments Cloned into M13 Vectors/(1983)/100, 468–500.

Schulz, G.E. & Schirmer/Principles of Protein Structure/(1979)/Table 1–2/Springer–Verlag New York.

Marotta, C.A. et al/Human β–Globin Messenger RNA III. Nucleotide Sequences Derived from Complementary DNA/The J. of Biological Chemistry/(1977)/252, 5040–5053.

Nagai, K. et al/Distal Residues in the Oxygen Binding Site of Haemoglobin Studied by Protein Engineering/Nature/(1987)/329, 858–860.

McCracken, A.A. et al/An Enrichment Selelction for Mutants Resulting From Oligonucleotide–Directed Mutagenesis of Double–Stranded DNA/(1988)/6(4), 332–339.

Sutcliffe, J.G./Complete Nucleotide Sequence of the Escherichia coli Plasmid pBR322/Cold Spring Harbor Symp. Quant. Biol/(1979)/43, 77–90.

Dickerson, R.E. & Geis, I./Evolution of the Oxygen Carriers/Hemoglobin: Structue, Function, Growth and Pathology/(1983)/Benjamin Cummings Publishig Co/California/Chapter 3/66–114.

Creighton, T.E./Proteins Structures and Molecular Principles/(1983)/W.H. Freeman and Company/New York/Figure 3–9.

Small, K.A. et al/A Rapid Method for Simultaneous Measurement of Carboxy–and Methemoglobin in Blood/J. of Applied Physiology/(1971)/31(1), 154–160.

Luisi, B.F. & Nagai, K./Crystallographic Analysis of Mutant Human Haemoglobins Made in Escherichia coli/Nature/(1986)/320, 555–556.

Tsukagoshi, N. et al/Cloning and Expression of a Thermophilic α–Amylase Gene from Bacilus stearothermophilus in Escherichia coli/Mol. Gen. Genet./(1984)/193, 58–63.

Tanaka, T. et al/Cloning of 3–Isopropylmalate Dehydrogenase Gene of an Extreme Thermophile and Partial Purification of the Gene Product/Biochem./(1981)/89, 677–682.

(List continued on next page.)

*Primary Examiner*—Robert A. Wax
*Assistant Examiner*—K. Cochrane Carlson
*Attorney, Agent, or Firm*—Henry P. Nowak; Marianne F. Novelli; Theresa A. Brown

[57] ABSTRACT

The present invention relates to a method for the production of a substantially protoporphyrin IX free hemoglobin solution comprising: rapidly heating a crude protoporphyrin IX-containing hemoglobin solution for a relatively short time and at a relatively high temperature to reduce protoporphyrin IX-containing hemoglobin to insignificant levels in said protoporphyrin IX-containing hemoglobin solution.

38 Claims, 12 Drawing Sheets

OTHER PUBLICATIONS

Genereaux, R.P. et al/Transport and Storage of Fluids/ Chemical Engineers' Handbook/(1973)/5th Edition/ McGraw–Hill/New York/6–29/6–32.

Lewis, M.K. & Thompson, D.V./Efficient Site Directed in Vitro Mutagenesis Using Ampicillin Selection/Nucleic Acids Research/(1990)/18(12), 3439–3443.

Commins, B.T. & Lawther, P.J./A Sensitive Method for the Determination of Carboxyhaemoglobin in a Finger Prick Sample of Blood/Brit. J. Industr. Med./(1965)/22, 139–143.

Van Assendelft, O.W. & Zulstra, W.G./Extinction Coefficients for Use in Equations for the Spectrophotometric Analysis of Haemoglobin Mixtures/Analytical Biochemistry/(1975)/69, 43–48.

Wensink, P.C. et al/A System For Mapping DNA Sequences in the Chromosomes of Drosophila Melanogaster/Cell/ (1974)/3, 315–325.

Benesch, R.E. et al/Equations for the Spectrophotometric Analysis of Hemoglobin Mixtures/Analytical Biochemistry/ (1973)/55, 245–248.

Taylor, J.D. & Miller, J.D.M./A Source of Error in the Cyanmethemoglobin Method of Determination of Hemoglobin Concentration in Blood Containing Carbon Monoxide/The Am. J. of Clin. Pathology/(1965), 43(3), 265–271.

Rodkey, F.L. et al/Spectrophotometric Measurement of Carboxyhemoglobin and Methemoglobin in Blood/Clin Chem./ (1979), 25(8), 1388–1393.

Collison, H.A. et al/Determination of Carbon Monoxide in Blood By Gas Chromatography/Clin. Chem./(1968), 14(2), 162–171.

Evelyn, K.A. & Malloy, H.T./Microdetermination of Oxyhemoglobin, Methemoglobin, and Sulfhemogbin in a Single Sample of Blood/The J. of Biological Chem.(1938)/126, 655–662.

De Boer, H.A. et al/The Tac Promoter: A Functional Hybrid Derived From The trp And lac Promoters/PNAS/(1983), 80, 21–25.

Christie, G.E. et al/Synthetic Sites for Trancription Termination and a Functional Comparison With Tryptophan Operon Termination Sites in Vitro/PNAS/(1981), 78(7), 4180–4184.

Farabaugh, P.J./Sequence of The lacI Gene/Nature/(1978), 274, 765–769.

Kunkel, T.A./Rapid and Efficient Site–Specific Mutagenesis Without Phenotypic Selection/PNAS/(1985), 82, 488–492.

Fogh–Andersen, N. et al/Diode–Array Spectrophotometry for Simultaneous Measurement of Hemoglobin Pigments/ Clinica Chimica Acta/(1987), 166, 283–289.

Johansson, M.B. & Wollmer, P./Measurement of Carboxyhaemoglobin By Spectro–Photometry and Gas Chromatography/Clinical Physiology/(1989), 9, 581–586.

Zijlstra, W.G. et al/Absorption Spectra of Human Fetal and Adult Oxyhemoglobin, Deoxyhemoglobin, Carboxyhemoglbin, and Methemoglobin/Clin. Chem./(1991), 37(9), 1633–1638.

Ownby, D.W. & Gill, S.J./Nonlinear Effects in Oxygen–Binding Reactions of Hemoglobin $A_o$/Biophysical Chemistry/(1990), 37, 395–406.

Asakura, T. et al/Relative Stabilities of Hemoglobins With Various Ligands/Blood/(1977), 50(5), 101.

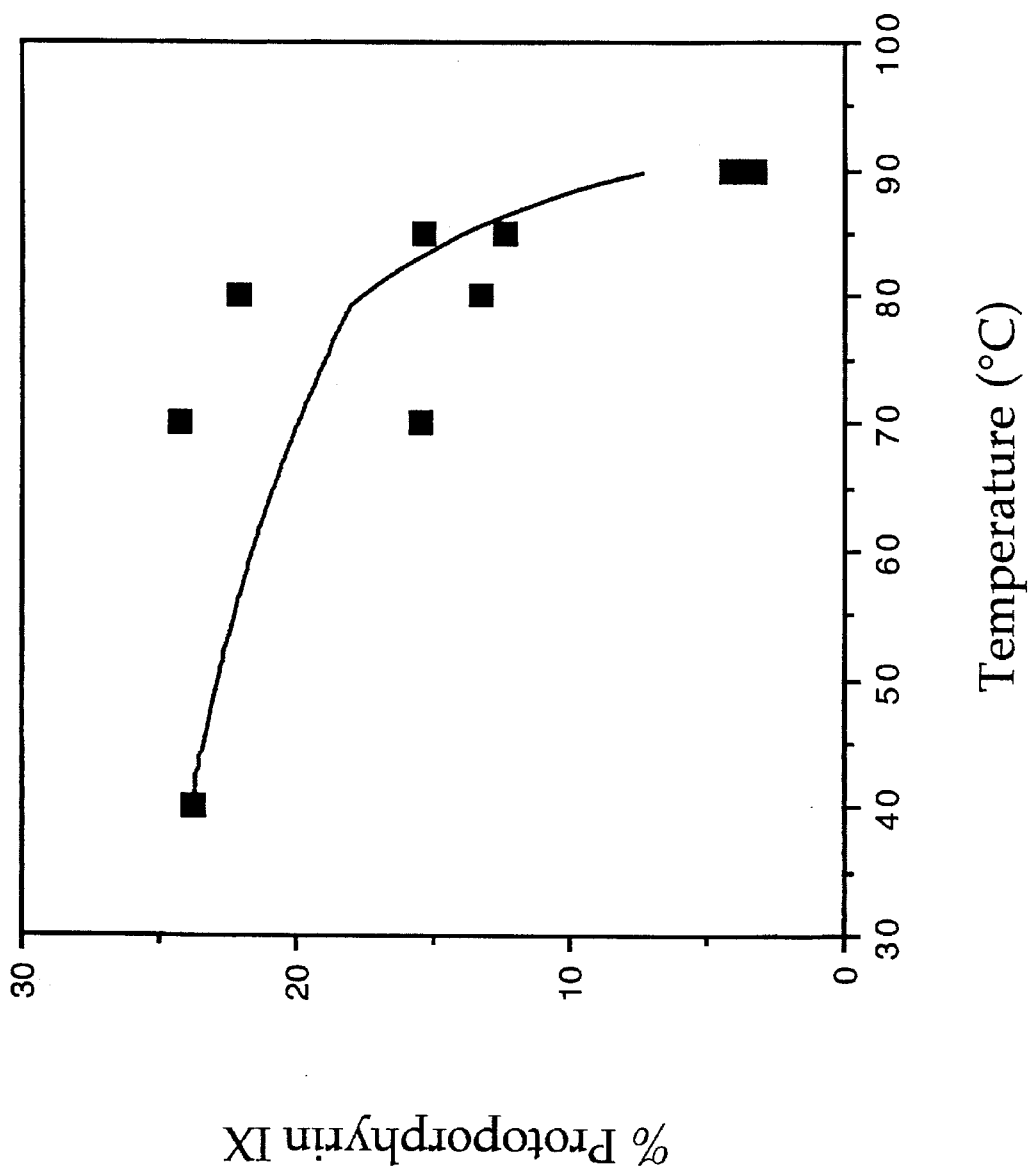

METHOD FOR THE RAPID REMOVAL OF PROTOPORPHYRIN FROM PROTOPORPHYRIN IX-CONTAINING SOLUTIONS OF HEMOGLOBIN

FIELD OF THE INVENTION

This invention relates to the field of purification of functional hemoglobin from contaminating hemoglobin and other proteins, particularly protoporphyrin IX-containing hemoglobin.

BACKGROUND OF THE INVENTION

It is not always practical or desirable to transfuse a patient with donated blood. In these situations, use of a red blood cell substitute is desirable. Such a product would need to transport oxygen, just as red blood cells do.

When patients lose blood, it is usually necessary to replace the entire fluid volume lost. However, it is not usually necessary to replace all of the lost hemoglobin. The primary goal of hemoglobin replacement therapy is to transport oxygen from the lungs to peripheral tissues. Hemoglobin administration also increases and maintains plasma volume and decreases blood viscosity. While many volume expanding colloid and crystalloid solutions are now marketed, none can transport oxygen. The only current therapy with this capability is human blood transfusion.

In clinical practice, patients suffering acute loss of small to moderate amounts of blood require only volume resuscitation. More severe blood loss requires both volume replacement and replacement of oxygen carrying capacity. Only in situations such as massive blood loss, is it necessary to replace other blood components, such as platelets and clotting factors.

The following risks and limitations are currently associated with human blood transfusions:

1) Risk of infectious disease transmission (i.e., human immunodeficiency virus (HIV), non-A and non-B hepatitis, hepatitis B, Yersinia enterolitica, cytomegalovirus, Human T-cell Leukemia Virus 1).

2) Immunologic risks (i.e., mild hemolytic or fatal transfusion reaction, immunosuppression, graft versus host reaction).

3) Need for typing and cross-matching prior to administration.

4) Availability of volunteer human donors.

5) Limited stability (unfrozen shelf life 42 days or less).

Genetic engineering techniques have allowed the expression of heterologous proteins in a number of biological expression systems, for example, insect cell lines, transgenic cells, yeast systems and bacterial systems. Expression of hemoglobin in particular has recently been demonstrated in transgenic pigs (Logan, et al., WO 92/22646), yeast (De Angelo et al., WO 93/08831 and WO 91/16349; Hoffman et al., WO 90/13645), and the bacterial E. coli system (Hoffman et al., WO 90/13645). Although expression of hemoglobin in these heterologous systems can be achieved at high levels (i.e., in the range of 5–10% of total cellular protein), purification of the final product to the extreme level of purity required for pharmaceutical use of hemoglobin remains difficult. Removal of contaminating isoforms of hemoglobin is particularly difficult in that these isoforms often co-purify with the desirable form of hemoglobin.

Hemoglobin (Hb) is a tetrameric protein molecule composed of two alpha and two beta globin units. In fully functional, normal or native hemoglobin, a heme molecule is incorporated into each of the alpha and beta globins. Heme is a large organic molecule coordinated around an iron atom. A heme group that is lacking the iron atom is known as protoporphyrin IX (PIX). PIX can be incorporated into one or more of the $\alpha$ and $\beta$ subunits of hemoglobin, but the PIX-containing subunit lacks the ability to bind and release oxygen.

Alpha and beta globin subunits associate to form two stable alpha/beta dimers, which in turn loosely associate to form the hemoglobin tetramer. Human hemoglobin Ao (also known as naturally occurring or native hemoglobin) is a heterotetramer composed of two alpha globin subunits ($\alpha_1$, $\alpha_2$) and two beta globin subunits ($\beta_1$, $\beta_2$). There is no sequence difference between $\alpha_1$ and $\alpha_2$ or $\beta_1$ and $\beta_2$. In the unoxygenated ("deoxy", or "T" for "tense") state, the subunits form a tetrahedron. The $\alpha_1\beta_1$ and $\alpha_2\beta_2$ interfaces remain relatively fixed during oxygen binding, while there is considerable flux at the $\alpha_1\beta_2$ and $\alpha_2\beta_1$ interfaces. In the oxygenated ("oxy" or "R" or relaxed) state, the intersubunit distances are increased. The subunits are noncovalently associated by Van der Waals forces, hydrogen bonds and, for deoxy Hb, salt bridges.

Because the alpha and beta globin sequences of hemoglobin are known, and efficient expression criteria have been determined, it is possible that any suitable biological protein expression system can be utilized to produce large quantifies of recombinant hemoglobin. Indeed, hemoglobin has been expressed in a number of biological systems, including bacteria, yeast and transgenic mammals. However, expression of functional hemoglobin in any cell requires not only the expression of the alpha and beta globin protein segments but also incorporation of the heme group into each of the alpha and beta subunits. If hemoglobin contains a protoporphyrin IX molecule rather than a heme group in any of the four subunits, functionality is reduced. If all of the prosthetic groups are protoporphyrin IX rather than heme, then the hemoglobin cannot bind or release oxygen and is completely non-functional.

Hemoglobin has been purified from a number of sources, including outdated red blood cells from both human and other mammalian sources (see for example Estep, U.S. Pat. Nos. 4,861,867 and 4,831,012; Rausch et al., U.S. Pat. No. 5,084,558), yeast systems (see for example, De Angelo et al., WO 93/08831 and WO 91/16349; Hoffman et al., WO 90/13645), transgenic systems (see Logan, et al., WO 92/22646) and bacterial systems (see for example Hoffman et al., WO 90/13645). Purification of hemoglobin from all the above sources generally requires at least some lyric step to liberate the hemoglobin from the cellular matrix, a low resolution fractionation step to remove contaminating soluble and insoluble proteins, lipids, membranes, etc. (e.g. filtration, centrifugation, pH dependent precipitation and long term (>1 hour) heating (see Estep U.S. Pat. No. 4,861,867), followed by some form of chromatographic final purification step known to those skilled in the art. The utilization of heat in the purification of hemoglobin from contaminating non-hemoglobin proteins is described in the Estep patent cited above. However, this fractionation of hemoglobin is useful only in the purification of already semi-pure hemoglobin solutions (99% by weight hemoglobin protein) that are in the deoxygenated (or T) state and that are derived from mammalian red blood cells heated for at least an hour, and can be considered a secondary purification step rather than an initial low resolution fractionation process. A clearly stated requirement of Estep is that the hemoglobin be in the deoxy state (hemoglobin which has no ligand, such as oxygen, bound to it) and that it be maintained in the deoxy or reduced state throughout the heating process by utilizing either chemical reductants or physical means (exposure to an inert gas).

When heterologous proteins are expressed in bacteria, heating of lysates of the bacterial cells, particularly E. coli lysates, is a common technique utilized in the purification of proteins derived from recombinant technology. However, heating of the material in solution after lysis of bacterial cells has generally been restricted to purification of known heat-stable proteins. This technique exploits the differences in thermal stability between most bacterial proteins and the heterologous protein. For example, in 1981 Tanaka and co-workers (Tanaka et al., (1981) Biochemistry 89: 677–682) expressed 3-isopropylmalate dehydrogenase from a thermophilic bacterium in E. coli, and purified this enzyme by heating the crude lysate for 10 minutes at 70° C. They note that this was a simple and effective procedure for rapidly purifying protein, and further state that "the enzymes of extreme thermophiles are stable in conditions where most of the proteins of E. coli cells used as host are heat denatured and precipitated . . . these observations suggest that any thermophilic enzyme can be purified with relative ease by cloning the genes in question into E. coli."

The heat purification of protein was again used by Beguin and others in 1983 (Beguin et al., (1983) Biochimie 65:495–500) to purify another heat stable protein (endoglucanase B) by a heat treatment at 60° C. for 15 minutes.

Tsukagoshi and co-workers in 1984 (Tsukagoshi et al., (1984) Mol. Gen. Genet. 193: 58–63) also purified a heat stable protein expressed in E. coli. However, they found that the thermal stability of the α-amylase that they were purifying was ligand dependent. The thermal stability in the absence of $Ca^{++}$ was approximately 10° C. lower than in the presence of $Ca^{++}$ (see FIG. 5, page 61). As a result, these workers added $Ca^{++}$ to the medium prior to heating to enhance stability of the enzyme and to recover greater activity. Moreover, this paper also demonstrates that the media conditions can be manipulated in order that the protein of interest is or becomes more thermostable than the contaminating E. coli proteins.

It is of note that these systems require both (a) heating of the lysate solutions for at least 10 minutes, and (b) a significant difference between the thermal stability of most of the contaminating proteins and the protein of interest.

Charm, U.S. Pat. No. 4,975,246, discloses a method for rapid heating (usually one second or less) of heat-sensitive materials using microwave energy in order to achieve pasteurization or sterilization of the material. There is no mention of using the method to achieve selective removal of contaminating materials.

Therefore, the present invention has the unexpected and heretofore unobserved characteristic of separating desired proteins from a protein matrix using rapid heating when the desired protein has similar thermal stability to some of the proteins in the protein matrix.

It is important to note that hemoglobin containing protoporphyrin IX rather than heme had not been obtained prior to this invention other than hemoglobin which has been chemically treated or modified specifically to result in protoporphyrin IX-containing hemoglobin. We have discovered that hemoglobin solutions, particularly those hemoglobin solutions resulting from recombinant production of hemoglobin, do contain significant levels of contaminating protoporphyrin IX-containing hemoglobin. Moreover, no mechanism for removal of such contaminating poorly functional hemoglobin has been available until now.

Surprisingly, we have discovered that hemoglobin containing protoporphyrin IX rather than heme can be separated from fully functional hemoglobin by subjecting mixtures of said hemoglobins to sufficient heat for a sufficient period of time.

SUMMARY OF THE INVENTION

The present invention relates to a method for the production of a substantially protoporphyrin IX free hemoglobin solution comprising: heating a crude protoporphyrin IX-containing hemoglobin solution for a sufficient time and at a sufficient temperature to reduce protoporphyrin IX-containing hemoglobin to insignificant levels of said protoporphyrin IX-containing hemoglobin solution. Preferably, the heating is rapid heating to a relatively high temperature, preferably for less than about several minutes at a temperature of from about 75° C. to about 90° C. Most preferably, the heating is by steam injection for about 10–11 seconds at 81° C. The heating also preferably occurs in the presence of carbon monoxide, which stabilizes the hemoglobin during heating.

It will be appreciated from the methods and descriptions described herein that the present invention can also be used to remove other contaminants besides protoporphyrin IX when such other contaminants have similar thermal stability to the thermal stability of protoporphyrin IX and the desired protein that is to be purified. The present invention therefore separates a desired protein from a protein matrix using rapid heating when the desired protein has similar thermal stability to some of the proteins in the protein matrix.

Another aspect of the present invention relates to essentially protoporphyrin IX-free hemoglobin solutions and pharmaceutical compositions, preferably such solutions obtained from purification of recombinant hemoglobin and particularly such recombinant hemoglobins obtained by the methods of the present invention.

To assist in the interpretation of the present patent, the following terms have the following meaning throughout this patent, including the claims appended hereto, unless otherwise indicated.

"Hemoglobin" or "hemoglobin-like protein" comprises one or more heterotetramers composed of (a) two alpha globin-like and two beta globin-like polypeptides, (b) one di-alpha globin-like and two beta globin-like polypeptides, (c) alpha globin-like and one di-beta globin-like polypeptide, (d) one di-alpha globin-like and one di-beta globin-like polypeptides, (e) one fused alpha/globin-like polypeptide and separate alpha and beta globin-like polypeptide or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers. In hemoglobin or hemoglobin-like protein, whether derived from natural or recombinant sources, in either the R or the T state, each alpha and beta globin-like polypeptide may contain a heme or protoporphyrin IX prosthetic group and therefore may have the ability to bind oxygen.

"Recombinant hemoglobin" means hemoglobin comprising alpha and beta globins at least one of which is obtained by expression of a globin gene carried by a recombinant DNA molecule, whether the hemoglobin is a conventional hemoglobin a mutant species, resulting in expression of a hemoglobin gene to produce a hemoglobin protein in a cell other than a cell in which such hemoglobin gene and/or hemoglobin protein is naturally found, i.e., the hemoglobin gene is heterologous to the host in which it is expressed. Therefore, the expression of any human hemoglobin gene in any cell other than a human red blood cell would be considered to be a recombinant hemoglobin. Moreover, the expression of a vertebrate hemoglobin in any species of invertebrate, or any vertebrate other than the vertebrate where the hemoglobin to be expressed is naturally occurring, would be considered a recombinant hemoglobin. Additionally, the expression of any naturally occurring hemoglobin mutant in any species other than the species in which it is naturally occurring, would be considered a recombinant hemoglobin. The expression of any non-naturally occurring mutant hemoglobin in any species would be considered a recombinant hemoglobin.

"Genetically fused hemoglobin" means a hemoglobin-like protein comprising at least one "genetically fused globin-like polypeptide" (globin pseudooligomer), the latter comprising two or more globin-like domains which may be the same or different. A di-alpha globin-like polypeptide is one which consists essentially of two alpha-globin-like polypeptide sequences (domains) connected by peptide bonds between the C-terminus of the first alpha-globin-like polypeptide (domain) and the N-terminus of the second alpha-globin-like polypeptide (domain). These two sequences may be directly connected or connected through a peptide linker of one or more amino acids; the term "peptide bonds" is intended to embrace both possibilities. Alpha globin chains crosslinked at the N- and C-termini other than by peptide bonds (e.g., by 4,4'-diisothiocyanatostilbene-2,2'-disulfonates, DIDS) are not di-alpha globins. The di-alpha globin-like polypeptide preferably is capable of folding together with beta globin and incorporating heme to form functional hemoglobin-like protein. The di-beta globin-like polypeptide is analogously defined. A di-alpha or di-beta globin-like polypeptide with a mutation in only one of the component domains is called "asymmetric".

"Liganded hemoglobin" means hemoglobin having at least one heme prosthetic group to which any ligand is bound. Common ligands include, but are not limited to, $O_2$, $CO_2$, NO, CO, HCN, and the like. Preferably the ligand is one that binds to the heme pocket. Common preferred ligands include, but are not limited to, $O_2$, CO, NO and the like.

"Oxyhemoglobin" means hemoglobin in which each of the functional oxygen binding sites has bound to it an oxygen molecule.

"Deoxyhemoglobin" or "unliganded hemoglobin" means any hemoglobin to which no ligand is bound to the alpha globin, the beta globin, and/or any functional heme prosthetic group.

"Protoporphyrin IX-containing hemoglobin" means any hemoglobin in which one or more heme prosthetic groups does not contain an iron atom.

"Protoporphyrin IX-containing hemoglobin solution" means a solution of hemoglobin that contains a detectable amount of protoporphyrin IX-containing hemoglobin, preferably as detectable by spectrophotometry. Preferably the amount of protoporphyrin IX-containing hemoglobin in the solution is significant. A significant amount of protoporphyrin IX-containing hemoglobin in a hemoglobin solution is when the amount of protoporphyrin IX-containing hemoglobin is any amount of protoporphyrin IX-containing hemoglobin that adversely affects the activity and suitability of the hemoglobin solution for a particular utility. Preferably, the amount of protoporphyrin IX-containing hemoglobin in a hemoglobin solution is at least about six percent (6%) of the total hemoglobin, more preferably, at least about seven percent (7%) of the total hemoglobin, more preferably at least about eight percent (8%) of the total hemoglobin.

"R-state hemoglobin" means the oxygenated ("oxy" or "R" or relaxed) state, in which the intersubunit distances are increased relative to the distances in T-state hemoglobin.

"T-state hemoglobin" means the unoxygenated ("deoxy", or "T" for "tense") state, in which the subunits form a tetrahedron. The $\alpha_1\beta_1$ and $\alpha_2\beta_2$ interfaces remain relatively fixed during oxygen binding, while there is considerable flux at the $\alpha_1\beta_2$ and $\alpha_2\beta_1$ interfaces.

DETAILED DESCRIPTION OF THE INVENTION

Figure 1A:
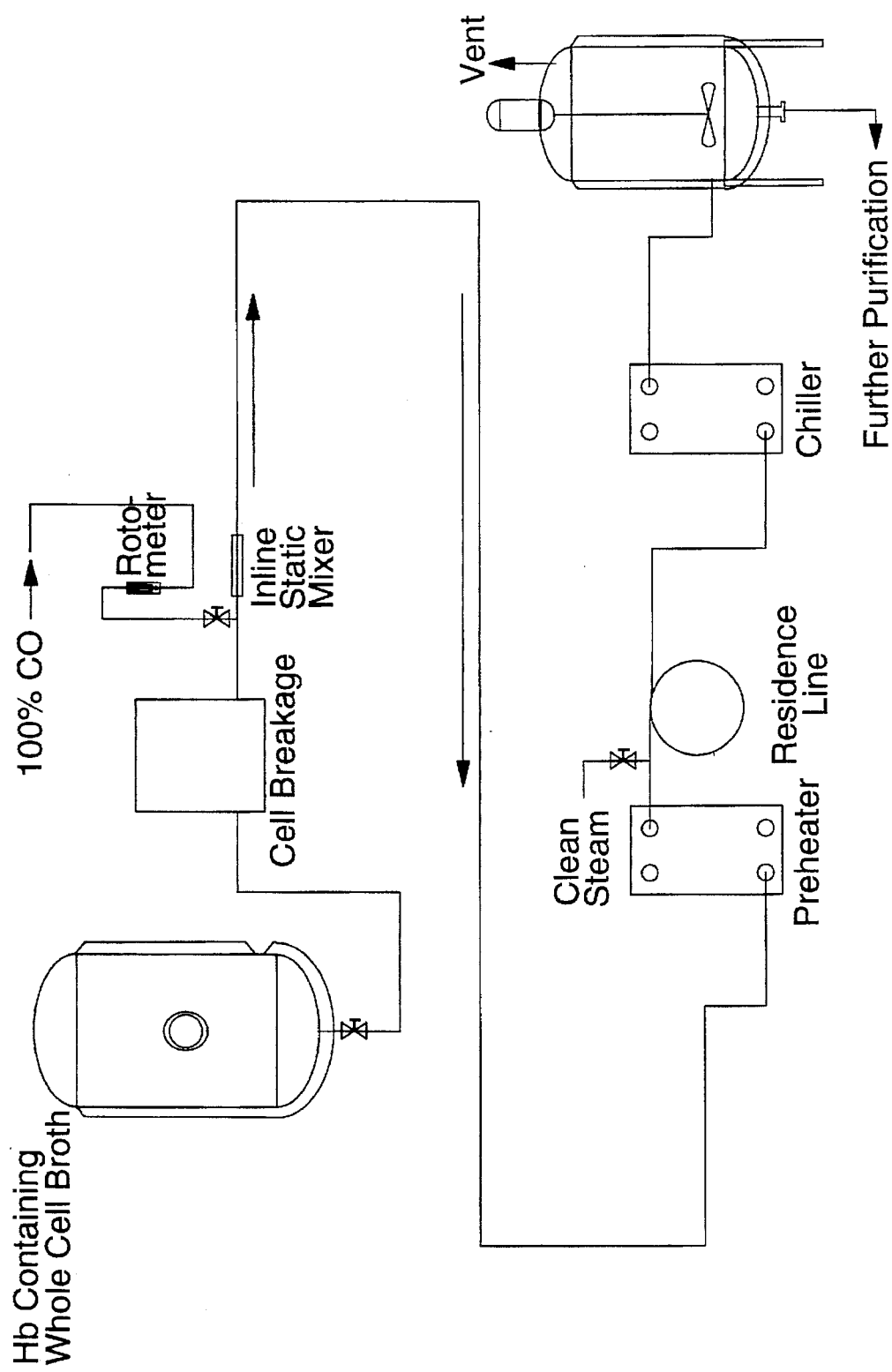
FIG. 1A shows a first configuration for rapid heating of a cell lysate under carbon monoxide gas throughout the heating process.

Hemoglobin can be purified from a number of sources well known to the art, including but not limited to outdated human red blood cells, bovine red blood cells and a number of non-red blood cell systems including, but not limited to, bacterial, yeast, and mammalian cells. In all these systems, one of the initial steps in the purification of functional hemoglobin from the cellular matrix is removal of variant forms of hemoglobins ("contaminating hemoglobins"). Such contaminating hemoglobins may be produced as a result of incorporation of one or more inactive heme groups into a given hemoglobin molecule. Removal of these contaminating hemoglobins, including protoporphyrin IX, is necessary to ensure product purity.

It is clear from the foregoing description that the present invention separates a desired protein from a cellular matrix using rapid heating when the desired protein, preferably a hemoglobin, has similar thermal stability to some of the proteins or other biological material ("contaminating proteins") in a cellular matrix. The heating is rapid enough to cause denaturation and removal of the contaminating protein without denaturation and removal of the desired protein, preferably a hemoglobin. Therefore, throughout the following description, which describes methods for removal of protoporphyrin IX-containing hemoglobin from a hemoglobin solution, the same methods can be employed to remove any protein or biological material from a desired protein (i.e., a desired hemoglobin) in a cellular matrix, (e.g., a cell lysate), so long as the thermal stability of the desired protein and the protein or biological material to be removed are nearly the same. Nearly the same thermal stability for two proteins or biological material means that heating of a solution of the two proteins or biological materials for at least an hour, preferably at least 5 minutes, more preferably at least 1 minute and more preferably at least 30 seconds, is required to result in denaturation of both proteins and/or biological materials.

In its most preferred embodiment, the present invention relates to a method for the production of a substantially protoporphyrin IX free hemoglobin solution comprising: heating a protoporphyrin IX containing hemoglobin solution for sufficient time and at a sufficient temperature to reduce protoporphyrin IX content of said protoporphyrin IX-containing solution.

The starting material for the method of the present invention is a protoporphyrin IX-containing hemoglobin solution. As previously mentioned, protoporphyrin IX-containing hemoglobin solution is a solution of hemoglobin that contains some protoporphyrin IX-containing hemoglobin. Usually the protoporphyrin IX-containing hemoglobin solution that is the starting material is a crude solution of hemoglobin that has undergone very little initial purification. A crude solution of hemoglobin for the purposes of this invention is a solution of hemoglobin that contains a substantial amount of hemoglobin not suitable for a specified purpose or utility ("contaminating hemoglobins") as well as other biological material, such as non-hemoglobin proteins, lipids, carbohydrates and the like.

Crude solutions of hemoglobin are readily available from a number of sources. Slaughter houses produce very large quantities of hemoglobin in the form of blood which is currently usually sold as an inexpensive fertilizer. If a particular species or breed of animal produces a hemoglobin especially suitable for a particular use, those creatures may be specifically bred for this purpose in order to supply the needed blood. Also, transgenic animals may be produced that can express a recombinant hemoglobin. Human blood banks must discard human blood after a certain expiration date. This also produces large quantities of hemoglobin. Techniques for the isolation of hemoglobin from blood are known per se (e.g., U.S. Pat. Nos. 4,831,012; 4,861,867 and 5,084,558). Any of the published or standard techniques may be used.

In addition to extraction from animal sources, the genes encoding subunits of a desired hemoglobin may be cloned, placed in a suitable expression vector and inserted into an organism, such as a microorganism, animal or plant, or into cultured animal or plant cells or tissues. These organisms may be produced using standard recombinant DNA techniques. Human alpha and beta globin genes have been cloned and sequenced by Liebhaber et al., Proc. Natl. Acad. Sci. USA (1980) 77;7054–7058 and Marotta et al., Journal of Biological Chemistry (1977) 252; 5040–5053, respectively. Techniques for expression of both wild-type and mutant alpha and beta globins, and their assembly into a hemoglobin, are set forth in U.S. Pat. No. 5,028,588 and PCT/US90/02654, PCT/US91/09624, and European Patent Application 87116556.9.

In most cases, crude solutions of hemoglobin initially involve hemoglobin that is contained within a cell. Therefore, the first step in the preparation of a crude solution of hemoglobin is to get the hemoglobins outside of the cell that has produced them. This can usually be accomplished by breaking open the cells, i.e., by sonication, homogenization or other cell breakage technique known in the art. Alternatively, the cells may be engineered to secrete the globins. After or concurrent with this first step, the various contaminating hemoglobins, including protoporphyrin IX-containing hemoglobin, can be removed as prescribed in the present invention by heating the protoporphyrin IX-containing hemoglobin solution.

Figure 1B:
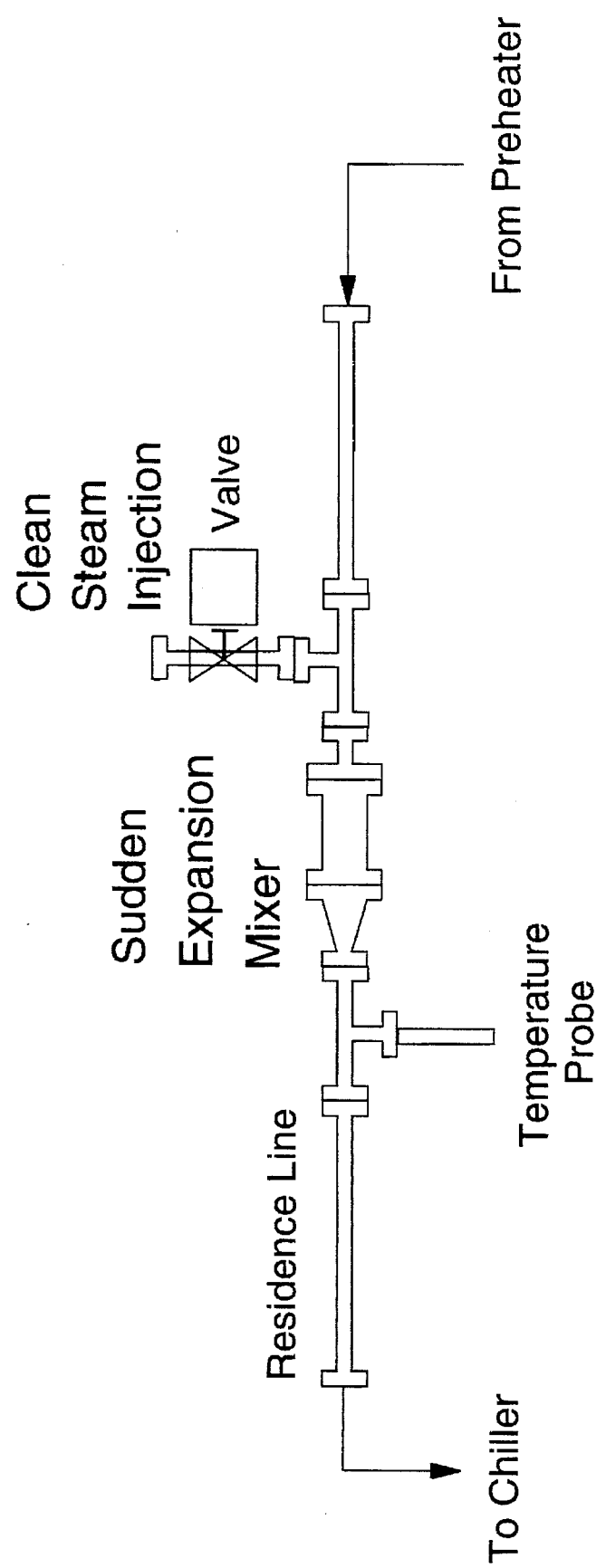
FIG. 1B shows a close up of steam injection for the configuration of FIG. 1A, including the location of the preferred sudden expansion mixer and the residence line, wherein the length of the residence line determines the retention time for heating.
Figure 2:
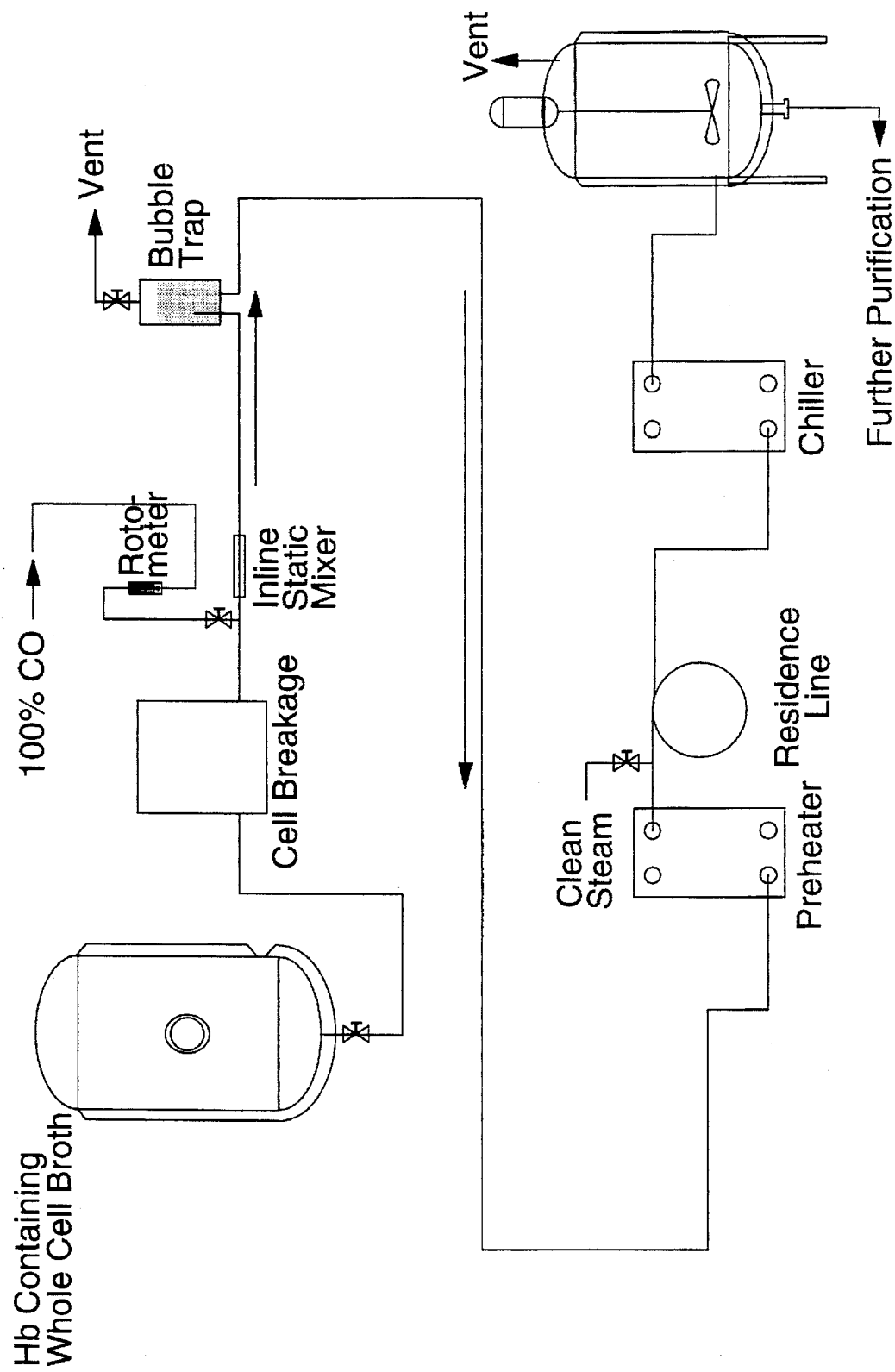
FIG. 2 shows a second configuration for rapid heating of a cell lysate with carbon monoxide exposure after homogenization and before preheating of the protoporphyrin IX-containing hemoglobin solution.
Figure 3:
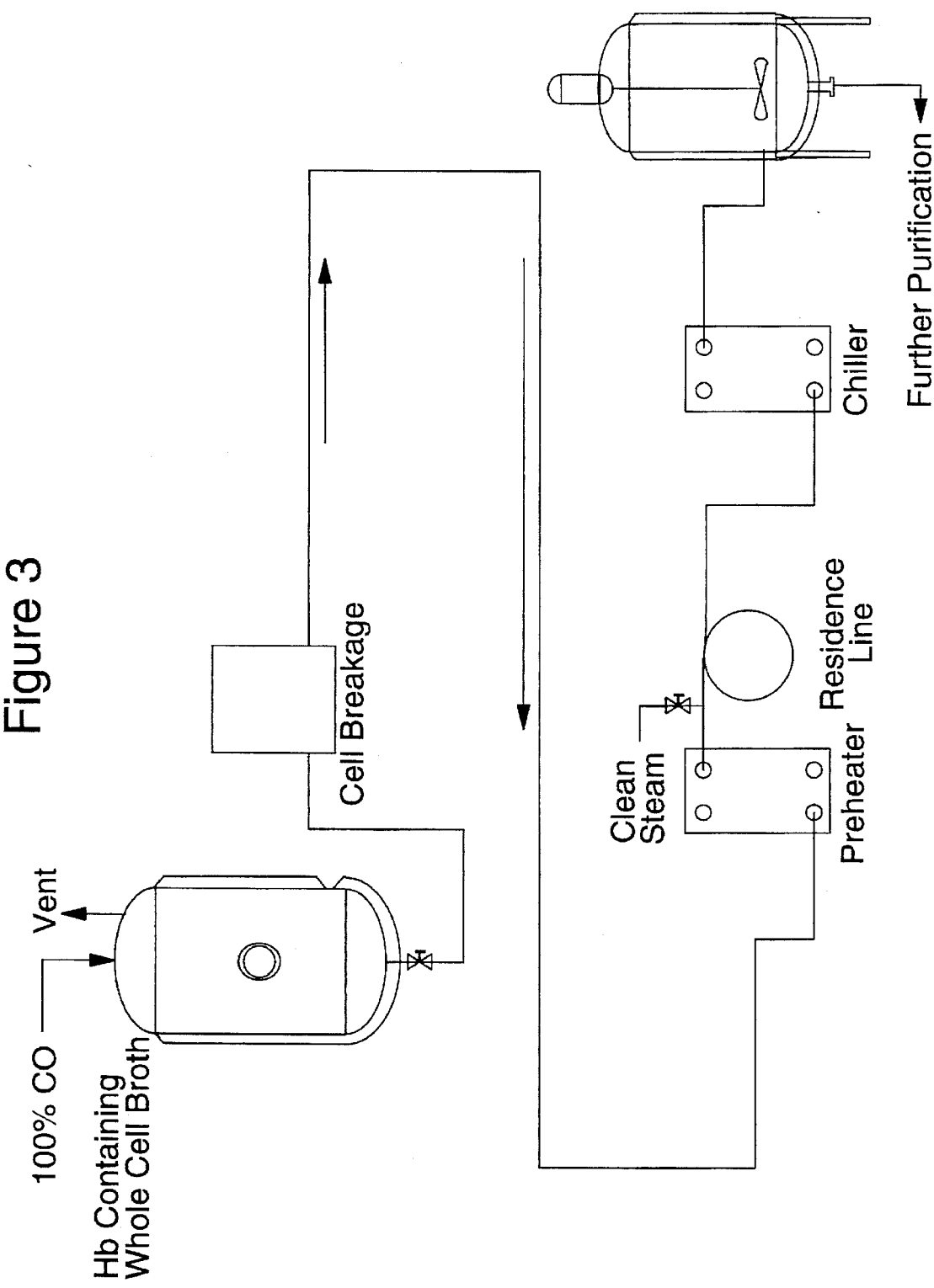
FIG. 3 shows a third configuration for rapid heating of a cell lysate with carbon monoxide exposure in a cell fermentation tank prior to homogenization of the cells.

Heating of the protoporphyrin IX-containing hemoglobin solution can be achieved by any means suitable for the removal of protoporphyrin IX-containing hemoglobin from the solution. These methods are known to those skilled in the art, and include, but are not limited to, tube and shell heat exchangers (e.g. Process Engineers Inc., Hayward, Calif.), plate and frame heat exchangers (e.g., APV Crepaco Inc., Rosemont, Ill.) steam injection heating, microwave heating (U.S. Pat. No. 4,975,246) and the like. Most preferably the crude hemoglobin solutions are heated by a means that heats the solutions extremely rapidly, particularly steam injection. Steam injection, for example, can occur by combining a steam stream with a stream of protoporphyrin IX-containing hemoglobin solution. Such steam injection can be accomplished using known engineering techniques, such as an in-line static mixer or a sudden expansion mixer, although the sudden expansion mixer is preferred because of the advantages it affords in avoiding fouling of the fluid stream line. Several illustrations of steam injection configurations are illustrated in FIGS. 1, 2 and 3 and others are known to those in the art, e.g., *Chemical Engineering Handbook*, 5th edition, McGraw-Hill, New York (1973) pages 6–29 to 6–32. Prior to the introduction of the high heat for the rapid heating, the protoporphyrin IX-containing hemoglobin solution may be prewarmed using a plate and frame heat exchanger (e.g., APV Crepaco Inc., Rosemont, Ill.).

Figure 4:
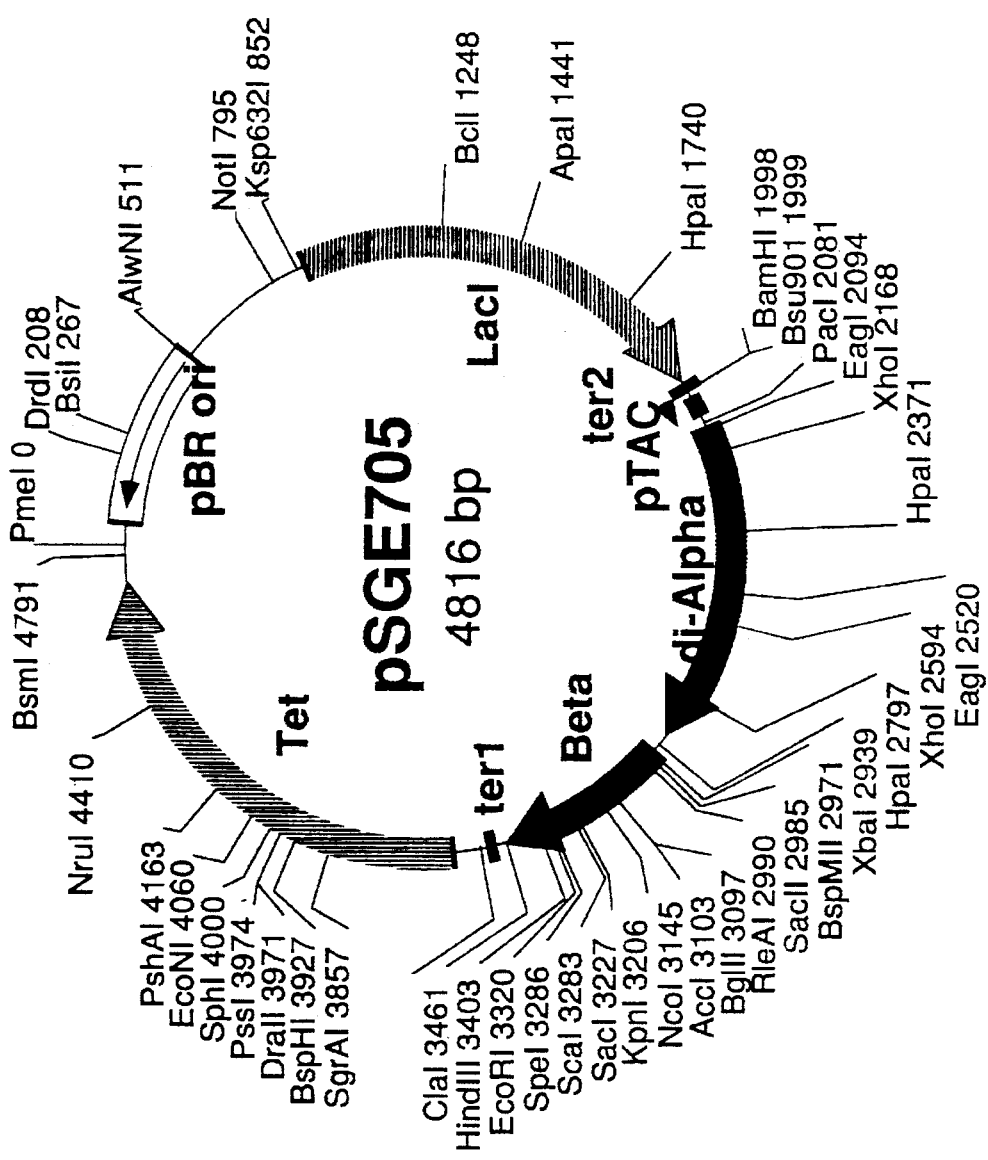
FIG. 4 shows a plasmid map of pSGE705, a plasmid used in the recombinant expression of a mutant hemoglobin, rHb1.1. The plasmid map includes relevant restriction sites.
Figure 5:
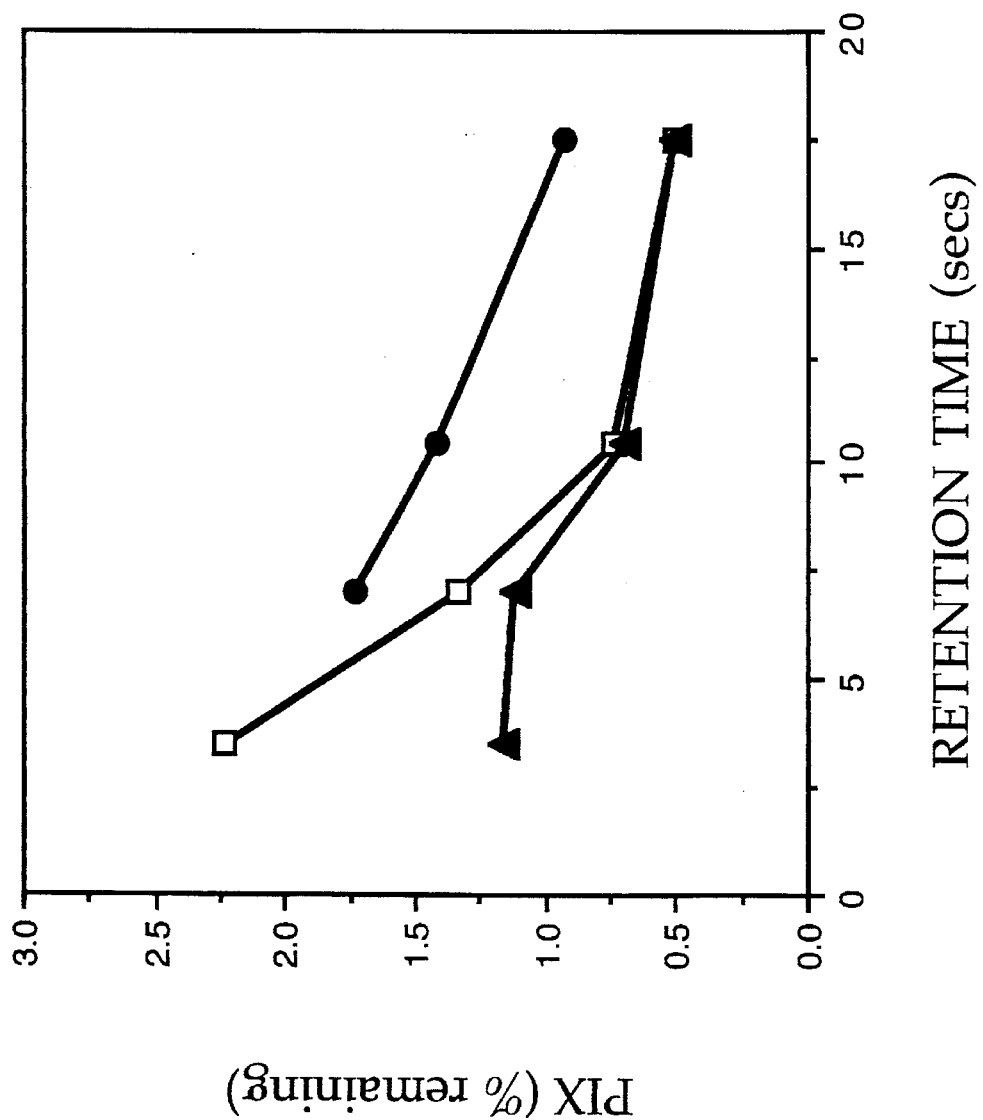
FIG. 5 shows a graph of protoporphyrin IX (PIX) remaining in a protoporphyrin IX-containing hemoglobin solution after heating as a function of heating retention times in seconds for three different heating temperatures: 78° C. (●), 80° C. (○), and 82° C. (▲).
Figure 7:
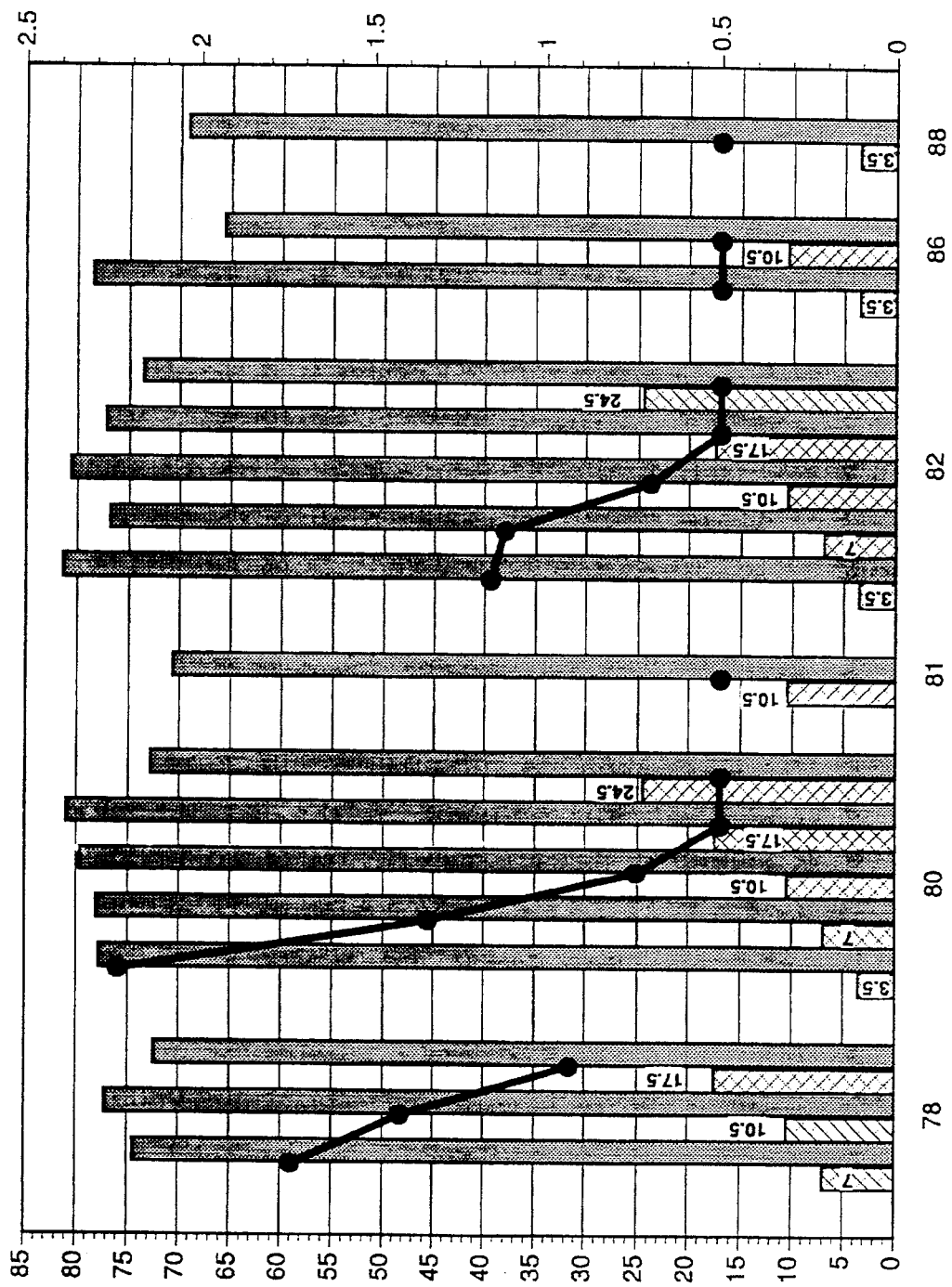
FIG. 7 shows a summary of fully functional hemoglobin yield in percent (gray bars with scale indicated on the left Y-axis) and protoporphyrin IX remaining (● with scale indicated on the right Y-axis) in a protoporphyrin IX-containing hemoglobin solution after heating by steam injection as described in Example 4. Values are presented for a number of temperatures (X-axis) and heating retention times (crosshatched bars with scale indicated on the left Y-axis).

Heating of the protoporphyrin IX-containing hemoglobin solution must occur for a sufficient time and at a sufficient temperature to reduce the protoporphyrin IX-containing hemoglobin to insignificant levels. The present invention shows that when crude hemoglobin solutions are exposed to heat for a surprisingly short period of time, significant protoporphyrin IX-containing hemoglobin is removed. Preferably, the heating time is less than about five minutes, more preferably less than about three minutes, more preferably less than about one minute, very preferably less than about 30 seconds, most preferably from about 5 seconds to about 15 seconds. In order to achieve removal of protoporphyrin IX hemoglobin from a protoporphyrin IX-containing hemoglobin solution in such a short time, it is necessary to heat the protoporphyrin IX-containing hemoglobin solution at a relatively high temperature. Such relatively high temperatures are temperatures above those to which hemoglobin is exposed in its natural environment, i.e., 37° C., preferably a temperature of at least about 55° C., more preferably at least about 65° C., more preferably at least about 75° C. more preferably at least about 80° C., very preferably from about 75° C. to about 90° C., even more preferably from about 80° C. to about 90° C., most preferably from about 80° C. to about 85° C. FIGS. 4 and 5 indicate that reduction of protoporphyrin IX-containing hemoglobin to levels below the preferred one percent level usually occurs only at longer retention times (greater than about 5 seconds) and at higher temperatures (greater than about 80° C.). The most preferred combination of temperature and time is to heat the protoporphyrin IX-containing solution for from about 10 to about 11 seconds (about 10.5 seconds) at a temperature of about 81° C. The selection of this most preferred combination of time and temperature is based on several considerations. First, from an engineering standpoint, retention times of less than about 5 seconds imposes significant constraints on the construction of a large scale production train. Second, it is desirable to reduce the protoporphyrin IX-containing hemoglobin to below detectable levels, which is less than about 0.5 percent as measured by the preferred measurement technique described herein. Third, it is desirable to make the retention time as small as is operationally feasible since the volume of protoporphyrin IX-containing solution during manufacturing of purified hemoglobin is usually very large. Therefore, a short retention time for heating allows faster processing time for large scale manufacturing volumes. As shown in FIG. 7, the retention time and temperature that meets these criteria without a significant loss of hemoglobin yield is a retention time of about 10.5 seconds and a heating temperature of about 81° C.

Insignificant levels of protoporphyrin IX-containing hemoglobin in a hemoglobin solution are those levels of protoporphyrin IX-containing hemoglobin that do not adversely affect the suitability and/or activity for a particular utility. Preferably, the amount of protoporphyrin IX-containing hemoglobin in a hemoglobin solution is less than about ten percent (10%) of the total hemoglobin, more preferably, less than about six percent (6%) of the total hemoglobin, more preferably less than about one percent (1%) of the total hemoglobin. Most preferably, the protoporphyrin IX-containing hemoglobin in a hemoglobin solution is below the detection limit for protoporphyrin IX in a given measurement technique. For example, the Zn capture column, HPLC, spectrophotometric method used in Example 1 of this invention has a detection limit of 0.2%.

During heating, the hemoglobin in the protoporphyrin IX-containing hemoglobin solution may be in either the liganded or unliganded state, but preferably is in either the fully liganded or fully unliganded state for selective removal of protoporphyrin IX without substantial loss of functional hemoglobin.

To ensure that the hemoglobin that is fully functional (e.g. containing four heme groups per hemoglobin tetramer) is either completely in the T state or completely in the R state, the crude protoporphyrin IX-containing hemoglobin solution can be first either deoxygenated (favoring the unliganded or T state) and/or sparged with a suitable non-oxygen gas (favoring the liganded or R state).

Deoxygenation can be accomplished by addition of an exogenous chemical reducing agent to the solution, such as dithionite or bisulfite, or by sparging of the solution with an inert gas such as nitrogen. Preferably, deoxygenation can occur by isolating the crude protoporphyrin IX-containing hemoglobin solution from contact with the atmosphere and allowing the reducing equivalents in a crude cell lysate to consume any available oxygen. This latter method is the preferred method of deoxygenation and is particularly suited to crude protoporphyrin IX-containing hemoglobin solutions that are obtained as a result of production of recombinant hemoglobin since the interior cell environment of most potential host cells, particularly bacterial and yeast cells, is highly reducing. Therefore, heating a crude protoporphyrin IX-containing hemoglobin solution, which by its very nature of being a crude solution of reducing cell components, will essentially provide a reducing environment without the need of adding exogenous chemical reducing agents.

Hemoglobin can be liganded with oxygen or non-oxygen ligands by mixing or sparging a crude protoporphyrin IX-containing hemoglobin solution with a suitable gas mixture. Non-oxygen ligands that can bind to hemoglobin include those recognized by Antonini and Brunori, *Hemoglobin and Myoglobin in Their Reactions with Ligands*, North Holland Publishing Company, Amsterdam (1971) 436 pages. Non-oxygen ligands are preferred because complete oxygen binding to hemoglobin to produce a fully liganded hemoglobin is difficult to achieve in the reducing environment that is present when the crude protoporphyrin IX-containing hemoglobin solution contains reducing cellular components. Preferably, the non-oxygen ligands are gases that bind to hemoglobin at the heme pocket and not the hemoglobin surface (e.g., such as $CO_2$). Those non-oxygen gases that bind at the heme pocket facilitate the transition to the R state. Examples of such preferred non-oxygen gases that bind at the heme pocket include, but are not limited to, carbon monoxide and nitric oxide. Preferably, the mixing of the crude protoporphyrin IX-containing hemoglobin solution with a non-oxygen gas is by sparging the crude protoporphyrin IX-containing hemoglobin solution with the non-oxygen gas after the hemoglobin-containing cells have been broken but prior to the heating (see FIGS. 1 and 2). Alternatively, the non-oxygen gas can be mixed with the hemoglobin-containing cells prior to harvesting of the cells (see FIG. 3). The preferred non-oxygen gas is carbon monoxide (CO), which can be essentially pure CO or a mixture of CO with other gases such as air, nitrogen, argon, helium or hydrogen (Scott Specialty Gases, Plumsteadville, Pa.). Preferably, the CO is essentially pure CO. The rate of mixing or sparging can be any rate that results in saturation of the crude protoporphyrin IX-containing hemoglobin solution with the CO or other non-oxygen gas. Therefore, the rate of sparging can be a specified flow rate of gas (e.g., 0.1–100 standard cubic liters per minute [sclm], preferably about 1 to about 50 sclm, more preferably about 1 to about 10 sclm, most preferably about 5 sclm) or until a specified amount of the hemoglobin is carboxyhemoglobin.

There exists an ability to quantitate various forms of hemoglobin, including methemoglobin (HbMet), carbonmonoxyhemoglobin (HbCO), oxyhemoglobin (HbO$_2$), reduced hemoglobin (Hb), protoporphyrin IX-containing hemoglobin (PIX) and total hemoglobin (HbTotal).

One method for measuring PIX, especially in a crude protoporphyrin IX-containing hemoglobin solution with many other species of hemoglobin, heroin and other fermentation products and components, is to separate out the hemoglobin species from other material using a zinc capture column, followed by separation of the various hemoglobin species using high performance liquid chromatography (HPLC), and detection and quantitation of PIX and other hemoglobin species by absorbance, preferably in the range of about 390–410 nm (See Example 6 for specific details).

The literature is also full of proposed and developed methods for the quantitation of other hemoglobin species described above, particularly methemoglobin (HbMet), carbonmonoxyhemoglobin (HbCO), oxyhemoglobin (HbO$_2$), reduced hemoglobin (Hb), and total hemoglobin (HbTotal), most particularly HbCO (Evelyn, et al., (1938) J. Biol. Chem. 126:655; Collison et al., (1968) Clin. Chem. 14:162; Johansson and Wollmer, (1989) Clin. Physiol. 9:581; Rodkey et al., (1979) Clin. Chem. 25;1388). The complexity of reported methods range from simple two wavelength ratios to multiple wavelength measurements requiring extensive calculations.

For example, Commins and Lawther (1965) Brit. J. Ind. Med. 22:139, utilize optical density of the HbCO peak at 420 nm by subtracting a baseline correction and the average of absorbances at 414 and 436 nm from the 420 nm absorbance value. Determination of the percentage HbCO relies on the preparation of a fully oxygenated sample of the unknown in order to set a reference point for the assay.

Fogh-Andersen et al. ((1987) Clin. Chim. Acta 166:283–289) also utilize a spectrophotometric technique, but instead employ six wavelengths and extinction coefficients for the species of interest at these wavelengths. The application of this technique requires precise knowledge of the extinction coefficients of the compounds of interest.

CO saturation can also be measured by use of the ratio of absorbances at 420 and 412 nm (Small (1971) J. Appl. Physiol. 31(1):154–160).

Because the number of potential hemoglobin species in a given sample is at least four, the use of two wavelength methods is inadequate to sufficiently discriminate between species unless the sample has been chemically pretreated to restrict the number of possible species, e.g. with sodium dithionite or potassium ferricyanide. Unfortunately each physical manipulation or pretreatment of a sample introduces uncertainty in the subsequent measurement, and in order to measure several species, several pretreatments are usually required. The optimal approach would require a minimum of sample manipulation and employ multiple wavelength measurements with computer assisted calculations.

An approach developed and preferred for the present invention is to employ multiple wavelength measurements in a fashion analogous to commercially available Hemoximeter instruments (Fogh-Andersen, et al. (1987) Clin. Chim. Acta 166:283–289) with the exception that extinction coefficients for various mutant hemoglobins can be used when the mutant hemoglobins are the desired hemoglobin to be purified from protoporphyrin IX-containing hemoglobin. This method uses application of a pseudoinverse matrix, derived from extinction coefficients of the hemoglobin species of interest at the selected wavelengths, to the measured absorbances of a given sample (see Example 5 for further details).

Consequently, the methods of the present invention can remove protoporphyrin IX-containing hemoglobin from a crude protoporphyrin IX-containing hemoglobin solution to result in a substantially protoporphyrin IX free hemoglobin solution. The substantially protoporphyrin IX free hemoglobin solution can then be subjected to further purifications techniques that are known in the art to further remove other hemoglobin and non-hemoglobin contaminants from the substantially protoporphyrin IX free hemoglobin solution to result in a hemoglobin solution that is very pure. The techniques for further purification can be, for example, as described in Estep, U.S. Pat. Nos. 4,861,867 and 4,8331,012; Rausch et al., U.S. Pat. No. 5,084,558 (human and mammalian sources), De Angelo et al., WO 93/08831 and WO 91/16349; Hoffman et al., WO 90/13645 (yeast sources), Logan, et al., WO 92/22646 (transgenic systems) and Hoffman et al., WO 90/13645 and Chivers and Belval, U.S. Ser. No. 08/097,273, filed Jul. 23, 1993 (bacterial systems).

For the purposes of the present invention, functional substantially protoporphyrin IX free hemoglobin solution is any non protoporphyrin IX-containing hemoglobin (desired or functional hemoglobin) that has the functionality necessary for a given utility. Utility of the purified hemoglobin solution can be, but is not limited to, reagent grade hemoglobin as a source of bio-available iron in dietary supplementation, as a highly purified molecular weight marker for laboratory applications, and most preferably as a modifier of the oxygen content of a solution, such as in the case of use of hemoglobin as an oxygen carrying solution that enhances the oxygen content of blood. The desired hemoglobin solution from which protoporphyrin IX-containing hemoglobin is removed can be either naturally occurring human hemoglobin or any of a variety of hemoglobin variants that are from other species, mutant hemoglobins, or hemoglobin-like molecules. The desired hemoglobin can be used alone in solution or can be part of a suitable pharmaceutical composition such as those described in Hoffman and Nagai, U.S. Pat. No. 5,028,588 and Chivers and Belval, U.S. Ser. No. 08/097,273, filed Jul. 23, 1993.

The structure of conventional hemoglobin is well known. We herewith incorporate by reference the entire text of Bunn and Forget, eds. *Hemoglobin: Molecular, Genetic and Clinical Aspects* (W.B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981), About 92% of the normal adult human hemolysate is Hb A (designated alpha2 beta2, because it comprises two alpha and two beta chains). The alpha chain consists of 141 amino acids. The iron atom of the heme (ferroprotoporphyrin IX) group is bound covalently to the imidazole of his 87 (the "proximal histidine"). The beta chain is 146 residues long and heme is bound to it at his 92.

The primary structure of a polypeptide is defined by its amino acid sequence and by identification of any modification of the side chains of the individual amino acids. The local bending of the chain is its secondary structure. The tertiary structure of the hemoglobin molecule refers to the steric relationships of amino acid residues, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the atoms of the molecule.

Normal hemoglobin in vivo is retained within erythrocytes, which have a life span of about 180 days. When erythrocytes age and die, they release hemoglobin into the bloodstream. There it dissociates into alpha-beta dimers. The dimers are cleared either by renal filtration, or as a result of haptoglobin binding. Hemoglobin may also be removed from serum by other mechanisms, such as by liver parenchymal cell uptake of free hemoglobin. The term "hemoglobin" as used in this application refers to a family of related molecules.

An alpha globin-like domain or polypeptide is a native alpha globin or a mutant thereof differing from the native sequence by one or more substitutions, deletions or insertions, while remaining substantially homologous (as hereafter defined) with human alpha globin, and still capable of associating with beta globin. A beta globin-like domain or polypeptide is analogously defined. Subunits of animal hemoglobins or mutants thereof which are sufficiently homologous with alpha or beta globin are embraced by the term "human alpha or beta globin-like domain or polypeptide." For example, the subunits of bovine hemoglobin are within the scope of these terms. The alpha- and beta-globin-like polypeptides may be referred to collectively as "globins". For the sake of convenience the term "polypeptide" may refer to a unitary chain or to a domain of a longer polypeptide chain. Preferably, the globin-like domain or polypeptide has the ability to incorporate heme.

It is also possible to provide an "alpha/beta-globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

Even though the di-alpha hemoglobin does not dissociate into dimers, it is still cleared from the bloodstream, albeit more slowly than is the case for normal hemoglobin.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha-globin-like polypeptides (or domains thereof) of the present invention have at least about 75% sequence identity with wild-type human alpha globin. However, a polypeptide of lesser sequence identity may still be considered "substantially homologous" with alpha globin if it has a greater sequence identity-than would be expected from chance and also has the characteristic higher structure of alpha globin and similar biological activity. By way of comparison, Artemia's heme-binding domains are considered homologous with myoglobin even though the primary sequence similarity is no more than 27%, as alignment of the heme-binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues.

Also, among the serine protease inhibitors, there are families of proteins recognized to be homologous in which there are pairs of members with as little as 30% sequence homology.

If the hemoglobin is to be produced by expression of recombinant DNA, the DNA can be engineered to produce desirable modified hemoglobins. Mutant substitute without the benefit of the red blood cell environment. Certain mutant hemoglobins with high oxygen affinity would be useful, for example, in delivery of oxygen to hypoxic tissues. Other mutants could be specifically designed to bind specific ligands other than oxygen for use in analytical assays or to scavenge and bind the non-oxygen ligand from a solution. By applying the standard techniques of site specific mutagenesis to the globin gene(s), (McCracken et al., (1988) Biotechniques 6(4); 332–339 and Zoller et al., Methods in Enzymology 100; 468–500 (1987) are recent examples) one can add, subtract or change any amino acid or combination of amino adds in the resulting globin chain.

Well over a hundred mutants of human hemoglobin are known, affecting both the alpha and beta chains, and the effect of many of these mutations on oxygen-binding and other characteristics of hemoglobin are known. Some preferred mutant hemoglobins include those disclosed in U.S. Pat. No. 5,028,588; PCT Patent Application WO 88/09179; PCT Patent Application WO 90/13645; PCT Patent Application 93/08842; and U.S. Pat. No. 5,173,426. The human alpha and beta globins themselves differ at 84 positions. In addition, interspecies variations in globin sequence have been extensively studied. Dickerson and Geis, (*Hemoglobin Structure, Function, Evolution and Pathology*, Benjamin Cummings Publishing Company, Menlo Park, Calif., (1983) Chapter 3) reported that in 1982, the 60 known vertebrate alpha globins had identical residues at 23 of their 141 positions, while for the 66 vertebrate beta globins considered, 20 of the 146 amino adds are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), *Glycera* (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), *Glycera* (125) and *Chironomus* (128).

Many of these differences may be misleading—variable amino acids may exhibit only "conservative substitutions" of one amino acids for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin-like protein, which preferably will reversibly bind oxygen. The following resources may be used to identify conservative substitutions (and deletions or insertions):

(a) data on hemoglobin mutants (over a hundred such mutants exist);
(b) data on sequence variations among vertebrate, especially mammalian, alpha globins and beta globins;
(c) data on sequence variations among vertebrate, especially mammalian, myoglobins;
(d) data on sequence variations between vertebrate and invertebrate globins, or among the invertebrate globins;
(e) data on the three-dimensional structures of human hemoglobin and other substantially homologous proteins, and molecular modelling software for predicting the effect of sequence changes on such structures; and
(f) data on the frequencies of amino acid changes between members of families of homologous proteins (not limited to the globin family). See, e.g., Tables 1–2 of Sculz and Schirmer, *Principles of Protein Structure* (Springer-Verlag: 1979) and FIG. 3–9 of Creighton, *Proteins Structure and Molecular Properties* (W. H. Freeman: 1983).

While the data from (a)–(d) is most useful in determining tolerable mutations at the site of variation in the cognate proteins, it may also be helpful in identifying which substitutions of amino acids are frequently conservative I. small aliphatic, nonpolar or slightly polar residues—Ala, Ser, Thr (Pro, Gly)
II. negatively charged residues and their amides—Asn Asp Glu Gln
III. positively charged residues—His Arg Lys
IV. large aliphatic nonpolar residues—Met Leu Ile Val (Cys)
V. large aromatic residues—Phe Tyr Trp The residues are parenthesized because of their special roles in protein architecture. Gly is the only residue without a side chain and therefore imparts flexibility to the chain. Pro has an unusual geometry which tightly constrains the particular folding. Note that Schulz and Schimer would merge I and II above. Note also that Tyr, because of its hydrogen bonding potential, has some kinship with Ser, Thr, etc.

In general, functionality is less likely to be affected by mutations at surface residues, at least those not involved in either the heme crevice or the subunit contacts. In addition, "loops" connecting alpha helices, especially the D loop of the alpha helix, as well as free amino or carboxy termini, are more tolerant of deletions and insertions.

Hemoglobin Ao is a heterotetramer composed of two alpha globin subunits ($\alpha_1, \alpha_2$) and two beta globin subunits ($\beta_1, \beta_2$). There is no sequence difference between $\alpha_1$ and $\alpha_2$ or $\beta_1$ and $\beta_2$. The subunits are noncovalently associated by Van der Waals forces, hydrogen bonds and, for deoxy Hgb, salt bridges. Hemoglobin is known to dissociate into $\alpha_1\beta_1$ and $\alpha_2\beta_2$ dimers, which are eliminated from the bloodstream by renal filtration. Intravascular retention of hemoglobin has been improved by e.g., chemical crosslinking of subunits of a single tetramer, or between tetramers.

As taught in U.S. Pat. No. 5,028,588 and PCT/US90/02654, it is possible to produce a pseudotetrameric hemoglobin in which two noncovalently associated subunits are replaced by a single pseudodimeric polypeptide with two oxygen binding domains, joined either directly or by a linker of one or more amino acids. This pseudodimeric polypeptide may be expressed from a suitable fused gene. Thus, two alpha globin genes may be fused into a "di-alpha globin" gene, or two beta globin genes into a "di-beta globin" gene, or alpha and beta globin genes into an "alpha beta" globin pseudodimer gene.

The advantage of fusing two or more globin chains together is that one can selectively mutate one but not both of the chains, as taught in Hoffman, et al., U.S. Ser. No. 789,179, filed Nov. 8, 1991, entitled Production and Use of Hemoglobins and Analogues Thereof.

Hemoglobin has been modified using many techniques in the past. Any of these techniques may be used to prepare a hemoglobin component of the invention that may be useful as a pharmaceutical composition. Examples of such modifications are found in U.S. Pat. Nos. 4,412,989, 4,301,144, 4,670,417, 4,321,259, 4,473,563, 4,710,488, 4,650,786, 4,336,248, 4,598,064, 4,600,531, 4,377,512 and 5,173,426 among others. Individual globin chains have been reassorted with modified forms to synthesize a semi-synthetic hemoglobin as well (Luisi et al., Nature (1986) 320:555–556 and Nagai et al., Nature (1987) 329:858–860). Chemically crosslinked hemoglobins, or mutant hemoglobins which genetically fuse the alpha subunits (di-alpha Hgb) or the beta subunits (di-beta Hgb), may increase intravascular retention by inhibiting haptoglobin binding. Other modifications such as polymerization of globin chains, glycosylation, pegylation, encapsulation in a liposome or cell membranes are also contemplated.

All references cited herein to books, journals, articles, patents and patent applications are hereby incorporated by reference for their relevant teachings.

EXAMPLES

The following examples are provided by way of describing specific and preferred embodiments of the present invention without intending to limit the scope of the invention in any way.

Example 1

Production of Protein Solution Containing Hemoglobin

A. Construction of a Bacterial System for the Recombinant Production of rHb1.1

Hemoglobin was produced by fermentation of one of the strains listed in Table 1 carrying either plasmid pSGE1.1E4 or pSGE705. The level of expression of rHb1.1 from the two plasmids was approximately the same, independent of the strain used, under the same fermentation conditions. Plasmid pSGE1.1E4 is described in (Hoffman et al, WO 90/13645). Construction of pSGE705 is described below.

Strain SGE127 carrying the plasmid pSGE1.1E4 is referred to as SGE128. Strain SGE800 carrying pSGE705 is SGE1353.

TABLE 1

Bacterial Strains

| STRAIN | GENOTYPE |
|---|---|
| SGE127 | F'traD36 lacI$^q\Delta$ (lacZ)M15 proBA +/$\phi$1A$^R$ $\phi$2A$^R$ recA1 thi gyrA96(NalR) endA $\Delta$(lac-proBA) hsdR17 relA1 supE44 |
| SGE800 | gyrA96(Nal$^R$) endA hsdR17 relA1 supE44,$\phi$1A$^R$, $\phi$2A$^R$, $\phi$3A$^R$ recJ |

$\phi$1A, $\phi$2A, and $\phi$3A are phage isolated from the fermentation area. $\phi$1A appears to be T5. $\phi$2A, and $\phi$3A have not yet been identified but are not T phage.

Materials.

pBR322, pUC19 and pNEB193 were purchased from New England Biolabs, Beverly, Mass. Oligonucleotides were synthesized on an Applied Biosystems DNA Synthesizer Model 392. The oligonucleotides used in preparing pSGE705 are listed in Table 3. Restriction endonucleases were purchased from New England Biolabs, Beverly, Mass. and used according to manufacturer's specifications. T4 DNA Ligase was purchased from either New England Biolabs, Beverly, Mass. or Gibco-BRL (Gaithersburg, Mass.) and used according to manufacturer's specifications. Pfu polymerase was purchased from Stratagene (La Jolla, Calif.) and used according to manufacturer's specifications.

Media used are described in J. H. Miller (*Experiments in Molecular Genetics*. Cold Spring Harbor Press, (1972) Cold Spring Harbor, N.Y.). and J. H. Miller (A *Short Course in Bacterial Genetics*. (1992) Cold Spring Harbor Press, Cold Spring Harbor, N.Y.). Acridine orange, ampicillin and kanamycin sulfate were purchased from Sigma Chemical Co. (St. Louis, Mo.). Tetracycline was purchased from Aldrich Chemicals (Milwaukee, Wis.).

Genetic and Molecular Biological Procedures.

Standard bacterial genetic procedures are described in J. H. Miller (*Experiments in Molecular Genetics*. (1972) Cold Spring Harbor Press, Cold Spring Harbor, N.Y.) and J. H. Miller (A *Short Course in Bacterial Genetics*. (1992) Cold Spring Harbor Press, Cold Spring Harbor, N.Y.). Standard molecular biology procedures were performed as described by Sambrook (Sambrook et al., *Molecular Cloning*. (1989) Cold Spring Harbor Press, Cold Spring Harbor, N.Y.).

Plasmid DNA Transformation.

DNA transformations were performed by the procedure described by Wensick (Wensick et al., (1974) Cell 3:315–325). Briefly, cells were grown to mid log phase and then pelleted, resuspended in an equal volume of 10 mM $MgSO_4$ and incubated on ice for 30 minutes. The cells were centrifuged and the pellet resuspended in ½ original volume of 50 mM $CaCl_2$ and placed on ice for 20 minutes. The cells were centrifuged again and then resuspended in 1/10 original volume of 50 mM $CaCl_2$. Plasmid DNA was added to the competent cells in a solution of 10 mM Tris-HCl pH 8.0, 10 mM $MgCl_2$ and 10 mM $CaCl_2$. The mixture was incubated on ice for 15 minutes and then incubated at 37° C. for 5 minutes. One milliliter of LB medium was added and the mixture incubated with shaking for 30–60 minutes. The culture was then centrifuged, resuspended in 0.1 ml of LB medium and plated on the appropriate selective medium.

Purification of DNA.

DNA fragments were purified from an agarose gel using the Geneclean system. (Bio 101, Inc. La Jolla, Calif.; method provided with product.) PCR products were prepared and cleaved with restriction endonucleases using the Double Geneclean system. (Bio 101, Inc. La Jolla; method provided with product.) Briefly, the PCR product was purified away from the PCR primers, then the PCR product was cleaved with restriction endonuclease(s) and purified from the restriction endonuclease and buffer. The PCR product was then ready for a ligation reaction.

TABLE 2.

Plasmids

| PLASMID | DESCRIPTION |
| --- | --- |
| pSGE1:1E4 | rHb1.1 expression plasmid containing di-alpha and beta genes |
| pSGE1.1E5 | like pSGE1.1E4 but ampicillin resistant instead of tetracycline resistant |
| pSGE490 | pUC19 lacI on a Bam HI-Hind III fragment |
| pSGE491 | pUC19 α on an Eco RI-Xba I fragment |
| pSGE492 | pNEB193 Ptac-α |
| PSGE493 | pUC19 β on an Xba I-Hind III fragment |
| pSGE500 | pUC19 α β on a Bam HI-Hind III fragment |
| pSGE504 | pSELECT-1 replace Sty I with a Pme I site |
| pSGE505 | pSGE504 rrnB T1 transcriptional terminator in the Eco RI-Cla I sites |
| pSGE507 | ColE1 ori and tet, 2213 bp |
| pSGE509 | ColE1 ori tet lacI, 3425 bp |
| pSGE513 | ColE1 ori tet lacI α β, 4386 bp |
| pSGE515 | ColE1 ori tet lacI diα β, 4812 bp |
| pSGE700 | pTZ18U + diα β from pSGE515 |
| pSGE705 | modified rHb1.1 expression plasmed, ColE1 ori, tet, lacI, di-alpha and beta genes |
| pTZ18U | a phagemid derivative of pUC19, for oligonucleotide directed mutagenesis |
| pDLII-91F | PGEM1 + α missing valine in 2nd position (Des-val) |
| pNEB193 | Like pUC19 but has more restriction sites in the multi cloning sites |
| pBR322 | ColE1 ori tet amp |
| pRG1 | pACYC177 lacI$^q$ |

TABLE 3

Oligonucleotides

| OLIGO | SEQUENCE (5'-3') | DESCRIPTION |
| --- | --- | --- |
| EV18 SEQ. ID #1 | CGGGAATACGGTCTAGATCATTAA CGGTATTTCGAAGTCAGAACG | C-term of α gene, Xba I site |
| EV27 SEQ. ID #2 | GATCCGAGCTGTTGACAATTAAT CATCGGCTCGTATAATGTGT GGAATTGTGACGGATAACAATTT CACACAGGAAATTAATTAATGCT GTCTCC | tac promoter sequence, Bam HI-Eag I sites |
| EV28 SEQ. ID #3 | GGCCGGAGACAGCATTAATTAAT TTCCTGTGTGAAATTGTTATCCGCTCAC AATTCCACACATTATACGAGCCGATGA TTAATTGTCAACAGCTCG | tac promoter sequence, Bam HI-Eag I sites, complement of EV27 |
| EV29 SEQ. ID #4 | TCGGATTCGAATTCCAAGCTGTTGG ATCCTTAGATTGAACTGTCTCCGGCCG | 5' end of α with Eco RI, Bam HI and |

TABLE 3-continued

Oligonucleotides

| OLIGO | SEQUENCE (5'-3') | DESCRIPTION |
|---|---|---|
| | ATAAAACCACCG | Eag I sites |
| EV30 | CGGAAGCCCAATCTAGAGGAA | 5' end of β with |
| SEQ. ID #5 | ATAATATATGCACCTGACTCCG GAAGAAAAATCC | Xba I site |
| EV31 | CCCGAAACCAAGCTTCATTAGTGA | 3' end of the β |
| SEQ. ID #6 | GCTAGCGCGTTAGCAACACC | gene with Hind III site |
| MW007 | TTTAAGCTTCATTAGTGGTATT | mutagenesis |
| SEQ. ID #7 | TGTGAGCTAGCGCGT | reverse primer replaces last three codons of β missing in pSGE515 |
| MW008 | CAGCATTAATTAACCTCCTTA | mutagenesis |
| SEQ. ID #8 | GTGAAATTGTTATCCG | reverse primer to optimize α ribozyme binding site (RBS) |
| MW009 | GGTGCATATATTTACCTCCTT | mutagenesis |
| SEQ. ID #9 | ATCTAGATCATTAACGGTATTTCG | reverse primer to optimize β RBS and remove second Bgl II site |
| TG14 | GGTTTAAACC | Pme I linker |
| SEQ. ID #10 | | |
| TG59 | GGCGAATAAAAGCTTGCGGCCGCG | Upstream of lacI |
| SEQ. ID #11 | TTGACACCATCGAATGGCGCAAAA CCTTTCGCGG- | gene, has a Hind III and a Not I site upstream of the promoter |
| TG60 | GGGCAAATAGGATCCAAAAAAAAG | Downstream side |
| SEQ. ID #12 | CCCGCTCATTAGGCGGGCTTTAT CACTGCCCGCTTTCCAGTCGGG | of lacI gene with the trp transcriptional terminator and a Bam HI site |
| TG62 | CCCCGAAAAGGATCCAAGTA | upstream primer |
| SEQ. ID #13 | GCCGGCGGCCGCGTTCCACTG AGCGTCAGACCCC | for pBR322 ori positions 3170–3148 with a Bam HI and a Not I site |
| TG63 | GGCGGTCCTGTTTAAACGCT | downstream |
| SEQ. ID #14 | GCGCTCGGTCGTTCGGCTGCGG | primer for pBR322 ori positions 2380–2404 with a Pme I site |

Annealing of oligonucleotides.

Complementary oligonucleotides were annealed according to the following procedure. Equimolar amounts of each oligonucleotide were mixed in 15–25 µl of 10 mM Tris-HCl pH 8.0/1 mM EDTA and incubated at 65° C. for 30 minutes. The sample was transferred to a 37° C. water bath for 30 minutes. Finally, the sample was incubated on ice for 60 minutes or in the refrigerator overnight.

Oligonucleotide directed mutagenesis.

Oligonucleotide directed mutagenesis was performed with the Muta-gene phagemid in vitro mutagenesis kit (Bio-Rad, Hercules, Calif.) according to manufacturer's instructions which are based on the method of Kunkel (Kunkel, T. A. (1985) Proc. Natl. Acad. Sci. USA 82:488; Kunkel et al., (1987) Methods Enzymol. 154:367). The rHb1.1 region of pSGE515 was cloned into pTZ18U (Bio-Rad, Hercules, Calif. or U.S. Biochemical, Cleveland, Ohio) on a Bam HI-Hind III fragment to create pSGE700. Three oligonucleotides, MW007, MW008 and MW009 were used to simultaneously introduce multiple changes in a single reaction.

Preparation of pBR322 ori.

PCR primers were designed to amplify the pBR322 origin of replication. These primers, TG62 and TG63, annealed to the positions 2380–2404 and 3170–3148 on the pBR322 DNA sequence (Sutcliffe, J. G. 1979. Cold Spring Harbor Symp. Quant. Biol. 43:77–90). The PCR product was digested with Not I and Pme I. The DNA fragment was purified according to the Geneclean procedure.

Preparation of tet gene fragment.

The source for the tet gene was pSELECT-1 (Promega Corp., Madison, Wis.). This plasmid has a number of restriction endonuclease sites, such as Bam HI, Hind III, Sal I and Sph I removed from the tet gene (Lewis and Thompson (1990) Nucleic Acids Res. 18:3439–3443). A Pme I linker was inserted into the Sty I site of pSELECT-1. This plasmid was designated pSGE504. Oligonucleotides TG71 and TG72 were annealed and ligated to the Eco RI-Cla I fragment of pSGE504. This plasmid, pSGE505, was shown to have the expected restriction endonuclease sites and to have lost the sites present in the multicloning site of pSELECT-1. pSGE505 was digested with Not I and Pme I. The 1417 bp fragment was purified according to the Geneclean protocol.

Preparation of lacI gene.

The lacI gene was isolated by amplifying the gene sequence from pRG1 (a gift from R. Garcia, Dana-Farber Cancer Inst., Boston) that carried the lacI gene. The PCR primers, TG59 and TG60 were designed to generate a wild type lacI promoter (Farabaugh, P. J. (1978) Nature 274:765), upstream of the gene and to place the trp terminator sequence (Christie et al., (1981) Proc. Natl. Acad. Sci. USA 78:4180–4184) downstream of the gene. The same step could be carried out using Y1089 (Promega) or chromosomal DNA from any *E. coli* strain carrying the lac region, such as MM294 (ATCC 33625.) The PCR product was gel purified and isolated according to the Geneclean procedure and cloned into Bam HI-Hind III digested pUC19 DNA to make pSGE490.

Construction of pSGE515.

PCR primers EV29 and EV18 were chosen to amplify the alpha gene from pDLII-91F (Hoffman et al., WO 90/13645). The purified PCR product was cleaved with the restriction endonucleases Eag I and Xba I.

To create a plasmid that contained P$_{tac}$-α, the alpha gene (from above) and the tac promoter, which was prepared by annealing EV27 and EV28, were mixed with Eco RI-Xba I cleaved pUC19 DNA. The mixture of the three DNA fragments, in approximately equimolar ratio, was treated with T4 DNA Ligase. After incubation the ligation mixture was used to transform SGE476 and ampicillin resistant transformants were selected. (Transformation into Strain MM294 (ATCC 33625) would yield equivalent results.) An isolate with the correct restriction endonuclease fragments (consistent with FIG. 4) was designated pSGE492. The α gene and the tac promoter DNA sequences were verified by DNA sequencing.

Primers EV30 and EV31 were used to amplify the β gene from pSGE1.1E4 by PCR. The purified β gene fragment was digested with Xba I and Hind III and then mixed with Xba I-Hind III digested pUC19 DNA and treated with T4 DNA ligase. The ligation mixture was used to transform competent SGE476 (equivalent to MM294, ATCC 33625) and transformants were selected on LB+ampicillin (100 μg/ml) plates. An isolate that contained the appropriate restriction endonuclease fragments (consistent with FIG. 4) was chosen and designated pSGE493. The β gene was confirmed by DNA sequencing.

The β gene was isolated from pSGE493 by restriction with Xba I and HindIII followed by purification according to the Geneclean method. This DNA fragment was then ligated to Xba I-Hind III restricted pSGE492 DNA and transformed into SGE713. (Any dam strain such as JM110 (ATCC 47013) or GM119 (ATCC 53339) could also be used.) An ampicillin resistant transformant that carried a plasmid that had the appropriate restriction fragments (consistent with FIG. 4) was chosen and designated pUC19αβ (pSGE500).

The Bam HI-Hind III fragment that contained the α and β genes of pSGE500 was purified according to the Geneclean method. An Xho I fragment that carried a portion of the di-α gene containing the glycine linker region was gel purified from pSGE1.1E5. pSGE1.1E5 (described in Hoffman et al., U.S. Ser. No. 789,179, filed Nov. 8, 1991) is a tetracycline sensitive analogue of pSGE1.1E4 (Hoffman et al., WO 90/13645), which could also have been used.

The pBR322 origin of replication region (pBR322 ori, above) was ligated to the tet gene fragment (above) and the ligation mixture was transformed into SGE476. (Transformation into MM294, above would yield equivalent results.) Tetracycline resistant transformants were selected and plasmid DNA was isolated and analyzed. An isolate that contained the appropriate restriction endonuclease fragments (consistent with FIG. 4) was chosen and designated pSGE507.

Next, pSGE507 and pSGE490 were digested with Bam HI and Not I and the appropriate fragments (consistent with FIG. 4) were purified. The two purified fragments were ligated together and the ligation mixture was used to transform competent SGE713. (Any darn strain could also be used; see above.) Tetracycline resistant transformants were selected, and plasmid DNA was isolated and analyzed. A plasmid that had the appropriate restriction fragments (consistent with FIG. 4) was chosen and designated pSGE509.

The purified Bam HI-Hind III fragment of pSGE500 that contained the α and β genes was ligated to Bam HI-Hind III digested pSGE509. The ligation mixture was used to transform pSGE713 (see above for equivalent strains) and tetracycline resistant transformants were selected and characterized. An isolate yielding the correct size plasmid with the expected restriction endonuclease fragments (consistent with FIG. 4) was chosen and designated pSGE513.

The Xho fragment of pSGE1.1E5 (described in Hoffman et al., U.S. Ser. No. 789,179, filed Nov. 8, 1991) that contained the di-α glycine linker sequence was ligated to Xho I digested pSGE513 to create a plasmid that contained the di-α gene. SGE753 was transformed with the ligation mixture and tetracycline resistant transformants were selected. (Transformation into SGE800 would have yielded equivalent results.) Isolates were screened to identify those that contained the Xho I fragment inserted into pSGE513 in the correct orientation (consistent with FIG. 4). An isolate that contained the correct configuration of the di-α gene, as determined by restriction endonuclease analysis with Eag I, was designated pSGE515.

Modification of pSGE515 to create pSGE705.

The DNA sequence record used to design PCR primers for the amplification of the β gene did not contain the C-terminal three amino acids. Oligonucleotide directed mutagenesis was used to add these nine nucleotides to the DNA sequence of the β gene. In the same reactions, modifications were introduced to optimize the ribosome binding sites for the di-α and β genes, and to remove a Bgl II site near the end of the di-α gene.

In the construction of the plasmid, one of the last steps was the modification of the ribosome binding sites to optimize the sequences. The following are the changes that were made with the oligonucleotides MW008 and MW009.

di alpha

```
before - CAATTTCAC---AGGAAATTAATTAATGCTG   SEQ. ID #15
         ||||||||| **||||**||||||||||||||
after  - CAATTTCACTAAGGAGGTTAATTAATGCTG   SEQ. ID #16
```

Four nucleotide changes, shown above, including the insertion of two nucleotides, were introduced with MW008 to optimize the ribosome binding site for di-alpha. (|-indicates identity, *-indicates a change)

beta

```
before - TAAa GATCTAGA---GGAAATAA-TATATGCAC    SEQ. ID #17
         ||| *||||||||***|||**|||*||||||||
after   - TAATGATCTAGATAAGGAGGTAAATATATGCAC    SEQ. ID #18
```

The six nucleotide changes shown above, including the insertion of four nucleotides, were introduced with MW009 to optimize the ribosome binding site for beta. The lower case "a" on the before strand was a T to A mutation in the construction of the alpha gene that introduced a Bgl II site into the sequence. This was removed so that there would only be a single Bgl II site in pSGE705. (l-indicates identity, *-indicates a change)

End of Beta

```
before - CTCGCTCAC---------TAATGAA    SEQ. ID #19
         |||||||||*********|||||||
after  - CTCGCTCACAAATACCACTAATGAA    SEQ. ID #20
```

MW007 introduced the coding sequence for the last three amino acids of the beta gene as shown above. (l-indicates identity, *-indicates a change)

Putative mutants were screened for loss of a Bgl II restriction endonuclease cleavage site (introduced by MW008). Seventeen of 24 had lost the site and were further characterized by DNA sequencing at the other two mutagenized sites. One of the 17 had incorporated all three modifications. These changes were verified by DNA sequencing and the rHb1.1 genes were cloned into Bam HI-Hind III digested pSGE509. An isolate that had the correct restriction endonuclease fragments was designated pSGE705.

A plasmid map of pSGE705 is shown in FIG. 4. The plasmid map indicates many of the restriction endonuclease cleavage sites. pSGE705 is smaller than its counterpart pSGE1.1E4, and the placement of its restriction sites facilitates modular alterations of the sequence. An unused antibiotic resistance marker was removed, and a promoter was added to the lacI gene that would allow tighter control of rHb1.1 expression.

A new sequence upstream of the α gene minimized the distance between the tac promoter (De Boer et al., (1983) Proc. Natl. Acad. Sci. USA 80:21–25) and the first codon of the alpha gene. The intergenic region between the di-α gene and the β gene was also designed to contain the minimum sequence that contained a restriction endonuclease site and the ribosome binding site for the β gene.

On Nov. 10, 1993 *E. coli* strains SGE127 and SGE800 were deposited with the American Type Culture Collection (ATCC Accession Numbers 69485 and 69484, respectively) under the terms of the Budapest Treaty on the International Recognition of the Deposit of Microorganisms for the Purposes of Patent Procedure and the Regulations thereunder (Budapest Treaty). This assures maintenance of a viable culture for 30 years from the date of deposit. The organisms will be made available by the ATCC under the terms of the Budapest Treaty, and subject to an agreement between Applicants and ATCC which assures unrestricted availability upon issuance of the pertinent U.S. patent. Availability of deposited strains is not to be construed as a license to practice the invention in contravention of the rights granted under the authority of any government in accordance with its patent laws.

B. Fermentations

The high volume six hundred liter fermentation procedures described below were used to obtain material for purification and functionality determinations.

Seed Stock

Seed stock was grown up in LB broth containing 10 g/L BactoTryptone™, 5 g/L yeast extract, 5 g/L NaCl, 0.2 g/L NaOH, 10 ug/mL tetracycline to an optical density of 1.5–1.7 at 600 nm. The solution was then made up to 10% glycerol and stored at −80° C. until required.

Fermentor Inoculum (500 mL broth in 2 L shake flasks)

To prepare the fermentor inoculum, seed stock was thawed, and 0.4 mL of seed stock were inoculated into 500 mL of a solution containing:

4.1 g/L $KH_2PO_4$
7.0 g/L $K_2HPO_4$
2.0 g/L $(NH_4)_2SO_4$
1.0 g/L $Na_3$ Citrate. $2H_2O$
154 mg/L $MgSO_4 \cdot 7H_2O$
up to 2.30 g/L of L-proline,
20 mL 10% yeast extract/L
10 mL 50% glucose solution/L
0.6 mL/L of sterile-filtered 125 mg/mL thiamine HCl dissolved in purified water
1 mL/L of 10 mg/ml tetracycline in an ~50% ethanol solution
2.5 mL of a trace metal solution containing:
    32.5 µg/ml $FeCl_3 \cdot 6H_2O$
    1.56 µg/ml $ZnCl_2$
    2.4 µg/ml $CoCl_2 \cdot 6H_2O$, 2.4 µg/ml $Na_2MoO_4 2H_2O$,
    1.22 mg/mL $CaCl_2 \cdot 2H_2O$,
    1.54 µg/ml $Cu(II)SO_4 \cdot 5H_2O$,
    0.6 µg/ml $H_3BO_3$,
    120 µl/ml HCl dissolved in purified water This culture was allowed to grow for 10 hours at 37° C. on a shaker. Four flasks were combined and used to inoculate the Seed Fermentors.

Seed Fermentor (10 L volume in 20 L Fermentor)

The entire fermentor inoculum was then asceptically transferred to a 20-liter fermentor containing 14 liters of a solution containing 2.19 g/L $KH_2PO_4$
3.97 g/L $K_2HPO_4$
2.19 g/L $(NH_4)_2SO_4$
0.29 mL/L polypropylene glycol-2000
12.2 mL/L of 50% glucose
10 mL/L of 125 mg/L thiamine HCl in purified water, sterile filtered solution
10.66 mL/L of 10 mg/L tetracycline in 50% ethanol solution,
12 mL/L of a post sterile addition solution containing:
    103 g/L $MgSO_4 \cdot 7H_2O$
    103 g/L $Na_3$-citrate.$2H_2O$
    170.5 g/L L-proline
226 mL/L of the trace metal solution described above.

The pH was maintained at 6.8 by addition of 15% to 30% $NH_4$ OH, dissolved oxygen was maintained at or above 30%, and 60% glucose was added throughout the growth period, sufficient to maintain low but adequate levels of glucose in the culture (0.5 g/L–10 g/L). Dissolved oxygen was maintained as close to 20% as possible. The culture was grown between 28° and 32° C. for approximately 12 hours prior to transfer to the 600 liter fermentor.

Production Fermentor

The entire seed fermentor inoculum was then aseptically transferred to a 600-liter fermentor containing approximately 425 liters of a solution of 2.02 g/L $KH_2PO_4$
3.6 g/L $K_2HPO_4$
2.02 g/L $(NH_4)_2SO_4$
0.1 mL/L polypropylene glycol-2000
100 mL/L of 50% glucose
10 mL/L of 125 mg/L thiamine HCl in purified water, sterile filtered solution
10 mL/L of 10 mg/L tetracycline in 50% ethanol solution
20 mL/L of a post sterile addition solution containing:
103 g/L $MgSO_4.7H_2O$
103 g/L $Na_3$-citrate.$2H_2O$
170.5 g/L L-proline
226 mL/L of the trace metal solution described above.

The pH was maintained at 6.8 by addition of 15% to 30% $NH_4$ OH, dissolved oxygen was maintained at or above 30%, and 60% glucose was added throughout the growth period, sufficient to maintain low but adequate levels of glucose in the culture (0.5 g/L–10 g/L). The culture was grown between 25° and 30° C. to an $OD_{600}$ ~10–40 prior to induction with 10–1000 µM IPTG. Upon induction of hemoglobin synthesis, the *E. coli* heme biosynthesis was supplemented by addition of hemin dissolved in 1N NaOH, either by addition of the total mass of hemin required at induction, or by periodic addition of heroin dissolved in 50 mM to 1M NaOH (e.g. one third of the total mass of hemin to be added to the fermentor was added at induction, another third was added after ¼ of the total time after fermentation had elapsed, and the last third was added half-way through the induction period). Total heroin added ranged from 50 to 300 mg/L. The fermentor was allowed to continue for 8–12 hours post-induction. At the end of this period, several 1 ml aliquots were removed from the broth for determination of hemoglobin production and protoporphyrin IX content.

C. Culture Harvest Breakage and Lysate Preparation

Cells were harvested by centrifugation at 10,000× g for 10 minutes or they were collected by filtration by cross-flow filtration with 0.2 µm membranes (e.g., Millipore Prostak). The cells were washed or resuspended to 30% (w/v) in a 25 mM Na-borate/2 mM EDTA buffer (pH 9.3). Lysozyme (final conc. 0.02 g/L) and protease inhibitor (e.g., 1 mM benzamidine or 50,000 U/L aprotonin) were added to the preparation. The suspended cells were allowed to incubate for 30 minutes at 30°–31° C., and then were broken by one or more passes through a homogenizer such as a Gaulin Model 30-CD™ Homogenizer operated between 10 and 14 Kpsi, Microfluidics Corp. Cell Disruptor Microfluidizer™ set at 13 Kpsi or a Niro homogenizer (Niro Hudson, Inc. Hudson, Wis.). The remainder of the process was performed either under a specified gas or, if no gas was specified, the procedure took place under ambient atmosphere. The temperature of the lysate was adjusted to 40° C. or the solution was utilized directly.

The lysed cells were then titrated to above pH ~6.8, preferably about 8.3, with 5N NaOH. Conductivity was adjusted to 30 Kmhos by addition of NaCl. The broken cell extract was clarified and the cell debris washed with borate buffer containing protease inhibitor (as above) by ultrafiltration. Since the hemoglobin product is soluble, it passed through the filtration membranes.

Example 2

Production of Functional Hemoglobin by Removal of Protoporphyrin IX from Crude Deoxy Hemoglobin Solutions with a Tube and Shell Heat Exchanger Protoporphyrin IX-containing hemoglobin is less thermostable than heme-containing hemoglobin molecules and differentially precipitates when subjected to rapid heating at high temperatures. Fermentations were performed as described in Example 1 with both *E. coli* strains SGE127 and SGE800 containing the plasmids pSGE1.1E4 and pSGE705, respectively. The two strains produced the same mutant hemoglobin and the fermentation products were essentially the same. Unwashed *E. coli* cells (100–300 L) were broken with a Niro homogenizer. The crude lysates were heated with a tube and shell design heat exchanger for 1.6–36 seconds at 70°–90° C. and material not heat treated is reported as 40° C., since the lysate reaches approximately that temperature through the Niro homogenizer. A flocculant aid, such as polyethyleneimine or Magnafloc 573™ (a poly-cationic flocculant made by CYTEC Industries, Indianapolis, Ind.) more preferable Magnafloc 573™, most preferably 5 ml of 50% Magnafloc 573™ solution/L of lysate was then added to the lysate and the lysate was clarified by centrifugation followed by depth filtration. Protoporphyrin IX and heme could not be accurately quantitated in the clarified lysate due to interference from other species (hemin and other fermentation products and components). As a result, the semi-purified hemoglobin containing both fully functional hemoglobin and protoporphyrin IX-containing hemoglobin were isolated from the lysate by zinc capture chromatography. Zinc captured material reflected the same proportion of protoporphyrin IX that was present in the lysate and could be used for quantitation of the protoporphyrin IX content of the crude lysate solution.

Zinc capture chromatography was performed using a chelating Sepharose Fast Flow 6B (Pharmacia, Inc., Piscataway, N.J.) column charged with 2 column volumes of 20 mM $Zn(OAc)_2$. The column was first equilibrated with 2 column volumes of 200 mM NaCl. Clarified *E. coli* lysate prepared from unwashed cells and brought up to 1–2 mM $Zn(OAc)_2$ was then loaded onto the column. The column was washed with 4 column volumes of 500 mM NaCl/20 mM Tris, pH 8.5, and then further washed with 4 column volumes of 20 mM Tris, pH 8.5. Captured hemoglobin was eluted from the column with 15 mM EDTA, pH 8.5. The column was then cleaned with 2 column volumes of 200 mM NaCl followed by 2 column volumes of 0.5N NaOH.

Figure 8:
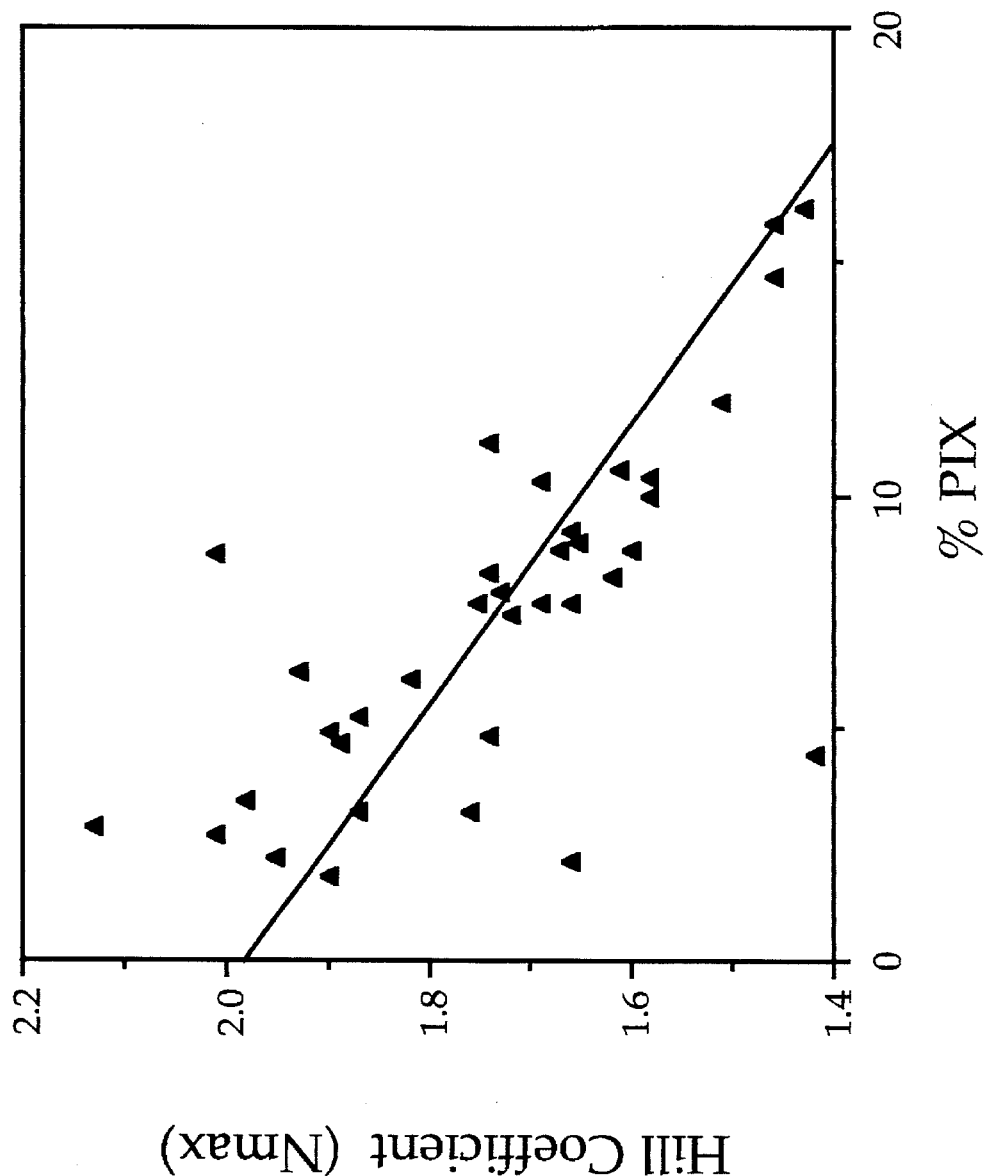
FIG. 8 shows a graph of Hill coefficient (Y-axis), which measures cooperativity (and is indirectly related to the functionality) of hemoglobin, versus protoporphyrin IX content of a protoporphyrin IX-containing hemoglobin solution.

The efficiency of the zinc capture step was approximately 95% with respect to hemoglobin. Relative amounts of protoporphyrin IX were determined by subjecting zinc captured material to C4 reverse phase HPLC, monitoring the elution at 405 nm, and integrating the area under the heme and protoporphyrin IX peaks. The relative amounts of protoporphyrin IX reported here are approximately 1.5-fold higher than measured by assays of protoporphyrin IX that utilized 396 nm as the monitoring wavelength. The data points in FIG. 8 represent a number of different fermentations treated under a number of different heating conditions. The trend for all of these fermentations and processing variables was that lower protoporphyrin IX content correlated with more functional hemoglobin. Heating conditions (time, temp, approach rate) were optimized to maximize loss of protoporphyrin IX-containing hemoglobin and minimize loss of heme-containing hemoglobin. The degree of cooperativity of solutions of recombinant hemoglobin (Hill coefficient

[n_{max}] as measured by Hemox analyzer) decreased linearly as the proportion of protoporphyrin IX-containing hemoglobin increased (FIG. 8).

Example 3

Figure 9B:
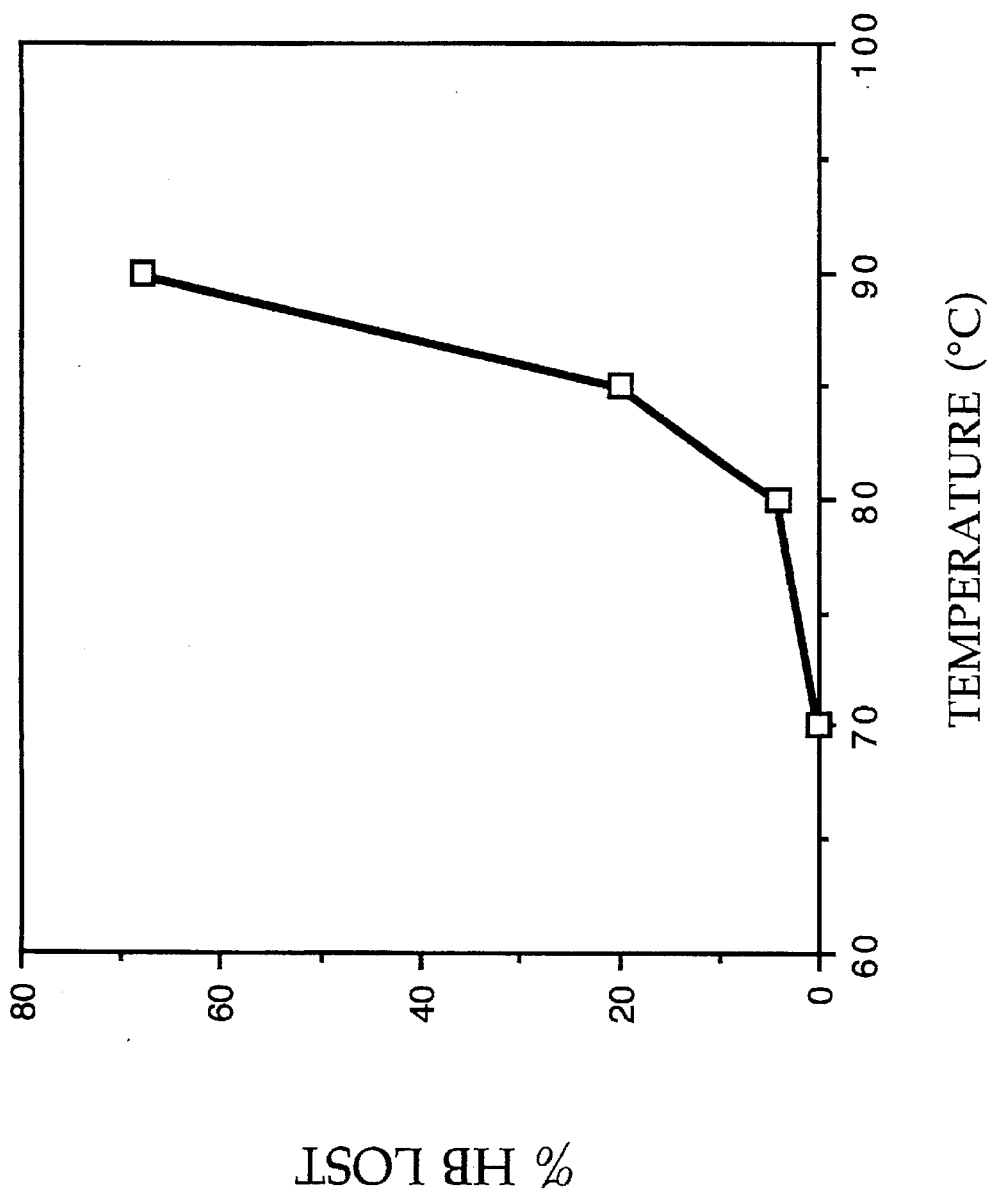
FIG. 9 shows the effects of heating temperature on the amount of protoporphyrin IX (PIX) remaining in a protoporphyrin IX-containing hemoglobin solution after heating (FIG. 9A) and on the amount of loss of total hemoglobin after heating (FIG. 9B). These values were determined using the heating method without carbon monoxide treatment before heating as described in Example 3

Effect of Temperature on the Efficiency of Protoporphyrin IX Removal with Rapid Heating under Deoxy Conditions For two fermentations with two different strains of *E. coli*, SGE127 and SGE800 containing the plasmids pSGE1.1E4 and pSGE705, respectively, the cells were broken with the Niro homogenizer (40° C.). No specific process steps were taken to ensure either deoxygenated or liganded conditions, but spectral analysis of the crude lysate solutions demonstrated that all the hemoglobin in the solutions was in the deoxygenated state. The crude *E. coli* lysate contained sufficient reducing power to maintain the solution in the deoxygenated state. Four portions of the crude solution were heated using a tube and shell heating apparatus (Process Engineers Inc., Hayward, Calif.) for 6 seconds at 70°, 80°, 85°, and 90° C. The final amount of protoporphyrin IX-containing hemoglobin in the lysate after heating decreased slowly from 40°–80° C., and rapidly between 80°–90° C. (FIG. 9A). These data demonstrate that *E. coli* lysates heated between 80°–90° C. had the most significant decreases in protoporphyrin IX-containing hemoglobin. However, heating the lysate between 85°–90° C. resulted in a loss of fully functional rHb1.1 hemoglobin (FIG. 9B).

Example 4

Figure 6:
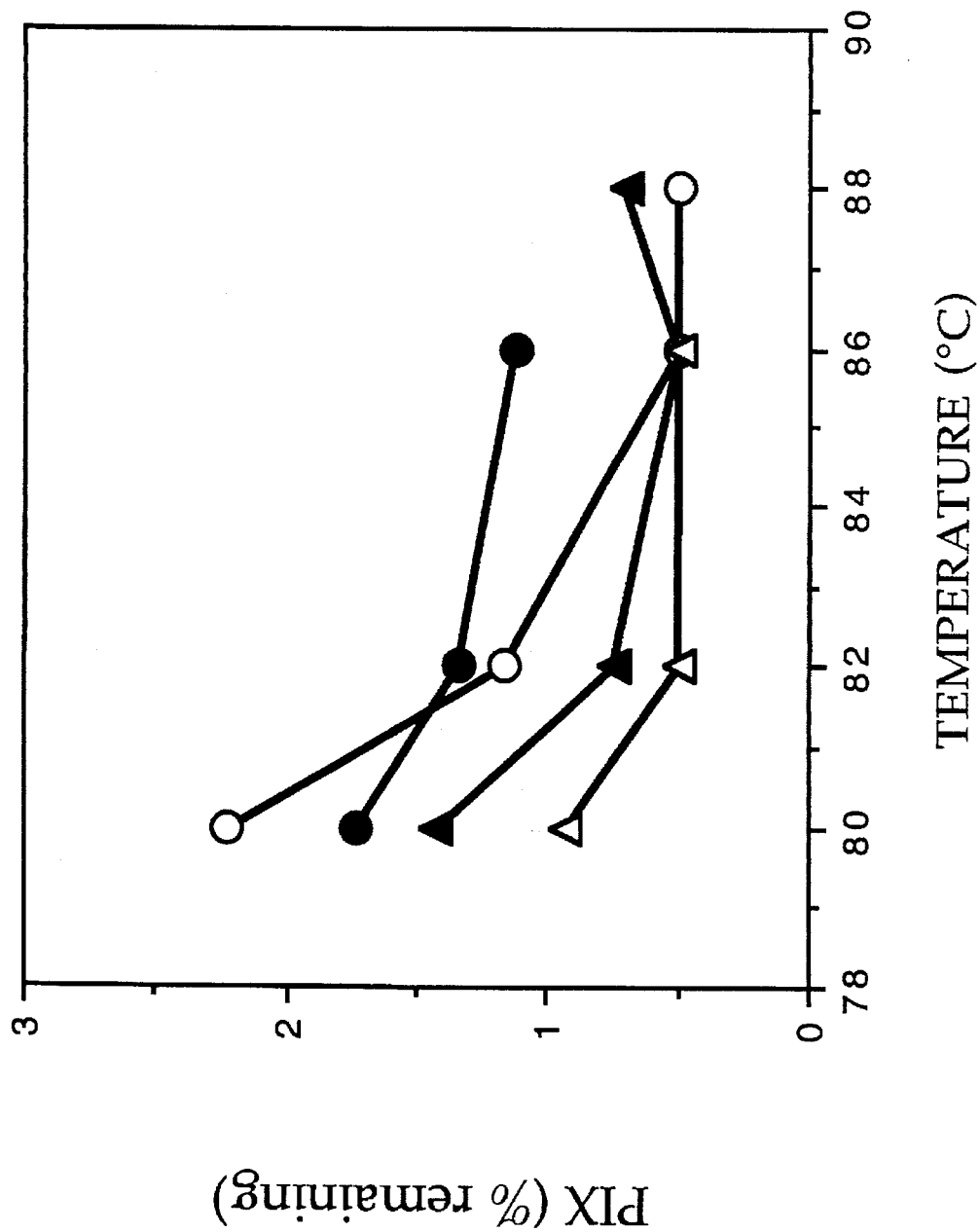
FIG. 6 shows a graph of protoporphyrin IX (PIX) remaining in a protoporphyrin IX-containing hemoglobin solution after heating as a function of temperature for four different retention times: 3.5 seconds (o), 7 seconds (●), 10.5 seconds (▲), and 17.5 seconds (△).

Efficiency of Protoporphyrin IX Removal with Rapid Heating under Liganded Conditions Hemoglobin produced by fermentations as in Example 1 with both *E. coli* strains SGE127 and SGE800 containing the plasmids pSGE1.1E4 and pSGE705, respectively, was sparged with 99.99% carbon monoxide at a flow rate of about 5 standard cubic liters per minute so that all available ligand binding sites in the solution were bound with carbon monoxide. After sparging, the crude protoporphyrin IX-containing hemoglobin solution was preheated in a plate and frame apparatus (APV Crepaco Inc., Rosemont, Ill.) to a temperature of 55° C. then heated for a length of time at a specific temperature by steam injection of the preheated crude protoporphyrin IX-containing hemoglobin solution as illustrated in the configuration of FIG. 1. Steam injection heating results in nearly instantaneous heating of the liquid. A variety of heating temperatures and retention times were examined. All combinations of time and temperature resulted in semi-purified hemoglobin solutions with significantly reduced protoporphyrin IX-containing hemoglobin concentrations as demonstrated in FIG. 7. FIG. 5 and FIG. 6 show the amount of protoporphyrin IX remaining as a function of retention time and temperature, respectively.

Example 5

Spectrophotometric Method of Measuring Carbonmonoxyhemoglobin

A. Spectrophotometric Method Using Pseudomatrices

A spectrophotometric method for the quantitation of hemoglobin species in aqueous solution was developed. Of particular importance is the ability to quantitate methemoglobin (HbMet), carbonmonoxyhemoglobin (HbCO), oxyhemoglobin (HbO$_2$), reduced hemoglobin (Hb) and total hemoglobin (HbTotal).

The chosen approach was to employ multiple wavelength measurements in a fashion analogous to commercially available Hemoximeter instruments (Evelyn, et al., (1938) J. Biol. Chem. 126:655; Collison et al., (1968) Clin. Chem. 14:162; Johansson and Wollmer, (1989) Clin. Physiol. 9:581; Rodkey et al., (1979) Clin. Chem. 25;1388) with the exception that rHb1.1 extinction coefficients would be used. This method uses application of a pseudoinverse matrix, derived from extinction coefficients of the hemoglobin species of interest at the selected wavelengths, to the measured absorbances of a given sample. The assumptions made for this method are:

1. Only the defined hemoglobin species are responsible for absorption at the measured wavelengths.
2. Observed absorbances at all wavelengths are the sum of the absorbances for each species at that wavelength.
3. The absorbance of each species follows Beer's Law, i.e. the absorption is a linear function of concentration.

Beer's Law may be represented as a series of simultaneous equations for several species:

$$\begin{bmatrix} A_1 \\ A_2 \\ \cdot \\ \cdot \\ \cdot \\ A_n \end{bmatrix} = \begin{bmatrix} \epsilon_{11} & \epsilon_{12} & \cdots & \epsilon_{1m} \\ \epsilon_{21} & \epsilon_{22} & \cdots & \epsilon_{2m} \\ \cdot & & & \\ \cdot & & & \\ \cdot & & & \\ \epsilon_{n1} & \epsilon_{n2} & \cdots & \epsilon_{nm} \end{bmatrix} * \begin{bmatrix} c_1 \\ c_2 \\ \cdot \\ \cdot \\ \cdot \\ c_m \end{bmatrix}$$

Where $A_1$ is the absorption at wavelength 1, $\epsilon_{11}$ is the extinction coefficient of species 1 at wavelength 1, $\epsilon_{12}$ is the extinction coefficient of species 1 at wavelength 2, etc., and $c_1$ is the concentration of species 1.

If the extinction matrix is not square it is not possible to generate a simple inverse matrix, instead a pseudoinverse matrix must be employed as follows:

$$A = \epsilon * c$$

$$\epsilon^T * A = (\epsilon^T * \epsilon) * c$$

$$[(\epsilon^T * \epsilon)^{-1} * \epsilon^T] * A = I * c = c$$

where $\epsilon^T$ is the transposed extinction matrix, $(\epsilon^T * \epsilon)^{-1}$ is the inverse matrix of the product of matrices T and $\epsilon$, and $[(\epsilon^T * \epsilon)^{-1} * \epsilon^T]$ is the pseudoinverse matrix.

All spectrophotometric measurements were performed using a 2 nm resolution HP8452 diode array spectrophotometer (Hewlett Packard, Palo Alto, Calif.) blanked against air. The majority of spectra were collected using a 0.1 mm pathlength quartz cell, however some experiments required the use of 1 mm and 1 cm pathlength quartz cells. Spectra were collected over a 190 to 820 nm window with a 5 second integration time. Extinction coefficients were determined using the product from a fermentation of *E. coli* strain SGE127 containing the plasmid pSGE1.1E4, a rHb1.1 standard, under conditions described below. No attempt was made to baseline correct the spectra for extinction coefficients at the time of collection. Subsequent sample spectra were collected employing the spectrophotometer's baseline correction routine specified to zero the average absorption between 700 nm and 800 nm. Spectral data was electronically transferred to Excel Spreadsheet files for manipulation and calculations.

Extinction Coefficient Determination:

In order to determine the pseudoinverse matrix for rHb1.1 at a given set of wavelengths it was necessary to establish the extinction coefficients for the species of interest at those wavelengths. The following sequence was employed to calculate the extinction coefficients for HbMet, HbCO, HbO$_2$ and Hb.

1. A two-fold excess of potassium ferricyanide (K$_3$Fe(CN)$_6$) based on hemes was added to an aliquot of the fermentation product and allowed to react for not less than 30 minutes prior to measurement. Spectra were then collected and assumed to be 100% HbMet. A diluted sample was measured with and without CO addition to determine the completion of oxidation.

2. A sample of recombinant hemoglobin was placed into a 5 mL syringe. The syringe was filled with 99% carbon monoxide, sealed and rotated for approximately 5 minutes. The gas was expelled and replaced with fresh carbon monoxide, sealed and rotated for approximately 5 minutes. The procedure was then repeated once more with carbon monoxide and the sample stored sealed with no headspace. Addition of carbon monoxide was assumed to not affect the HbMet content.

3. A sample of the fermentation product was processed as in sample 2 with the exception that oxygen was used in place of carbon monoxide. The addition of oxygen was assumed to not affect the HbMet or HbCO content.

4. A 100 fold excess of sodium dithionite (Na$_2$S$_2$O$_4$) based on hemes was added to an aliquot of the fermentation product and allowed to react for 5 minutes prior to measurement. The addition of the dithionite was assumed to result in reduction of HbMet and HbO$_2$ to Hb but to not affect the HbCO content.

The original HbTotal concentration was taken from Cyanomethemoglobin analysis as 50.79 g/L. The original HbMet content was 5.64%, as determined by the Evelyn-Malloy method. The original HbCO content was taken from CO gas chromatography analysis as 0.82%. Reduced hemoglobin content was assumed to be 0% for all samples except the dithionite reduction.

A total of 30 spectra were gathered for each HbMet, HbCO and HbO$_2$, and 10 spectra for Hb. In order to assure a zero baseline the average absorption from either 700–800 nm or 790–810 nm for each spectrum was calculated and subtracted from all absorption in that spectrum. The rationale for evaluating two different correction windows was to ensure that no meaning absorptions were lost due to the background correction. Subsequent calculations were performed in parallel to establish the effect of the correction window. All spectra, within a correction window set, for a given species were averaged at each wavelength. Accommodating for the dilution associated with the addition of K$_3$Fe(CN)$_6$ and Na$_2$S$_2$O$_4$ and the mixed nature of some samples the extinction coefficients for each species were calculated in units of $$\frac{OD*L}{g*0.1\,mm} \text{ and } \frac{OD*L}{4\,mmol*cm}.$$

Figure 10:
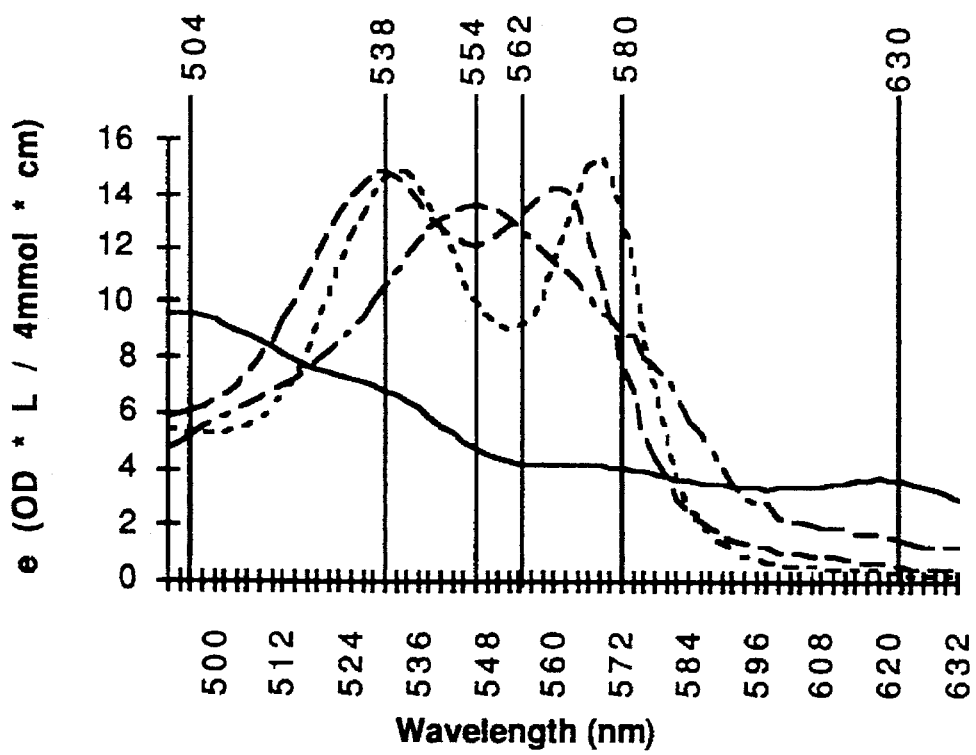
FIG. 10 shows the millimolar extinction coefficients of various hemoglobin species of recombinant hemoglobin 1.1 (rHb1.1) methemoglobin (HbMet)(_____); carbonmonoxy hemoglobin (HbCO)(-----); Oxyhemoglobin (HbO$_2$)(·····); and total hemoglobin (-·-·-·-).

Calculated values were then compared to literature values for wild type HbA$_o$ (Zijlstra et al., (1991) Clin. Chem. 37:1633; van Assendelfdt and Zijlstra (1975) Anal. Biochem. 69:43; Benesch et al., (1973) Anal. Biochem. 55:245). An overlay of the extinction coefficients for the 4 species is shown in FIG. 10.

Pseudoinverse matrices were prepared for the following extinction coefficient sets and for each correction window:

1. All measured wavelengths 500–640 nm including Hb (All Wave/Hb)
2. Six specified wavelengths including Hb (6 Wave/Hb)
3. All measured wavelengths 500–640 nm excluding Hb (All Wave/no Hb)
4. Six specified wavelengths excluding Hb (6 Wave/no Hb)

The six specified wavelengths were chosen to be 504 nm, 538 nm, 554 nm, 562 nm, 580 nm, and 630 nm. Selection of these wavelengths was based upon the relative extinction coefficients of the four species of interest. Each wavelength is either a point of matrix separation of all species or an isosbestic point of two species with maximal separation of the remaining two species. The rationale to evaluate the inclusion and exclusion of the Hb species was based upon some preliminary experiences. One aspect of the pseudoinverse matrix solution is that mathematically negative concentrations are allowed, however physically a negative concentration is difficult to interpret. Because the concentration of Hb is usually quite small in normal sample preparation it periodically displays a negative concentration. This could be handled by allowing negative concentrations with the understanding that they represent a minimal contribution to the total hemoglobin in solution, setting negative concentrations to 0, or by excluding Hb from the original calculations.

Initial experimentation was designed to determine the effect of species concentration and distribution on resulting calculations. In all cases multiple spectra were collected for each condition. Matrix multiplication was then performed with each pseudoinverse matrix described above to determine the most effective pseudoinverse matrix. Comparisons of pseudoinverse matrix performance was based upon average recovery of theoretical species concentration.

HbCO Content:

A sample of purified rHB1.1 was carbon monoxide treated as described above and mixed with untreated material in defined proportions. The original sample was evaluated for HbMet content using the Evelyn-Malloy method. Each mixture was analyzed in triplicate by GC to determine the actual carbon monoxide content.

Each sample was also spectrophotometrically measured in triplicate in a 0.1 mm pathlength cell without dilution. Spectral data was then used to calculate apparent concentration of all species using the described pseudoinverse matrices. Several features of the analysis are noteworthy:

1. The ability of all matrices to correctly predict the amount of HbCO is good over the complete range. Accuracy appears to be best at high and low levels of HbCO with a slight under estimation (~5%) at intermediate levels. The best performance was observed with the All Wave/Hb matrix.
2. Increasing HbCO levels did not appear to affect the apparent HbMet content.
3. Increasing HbCO levels resulted in an apparent increase in the total hemoglobin content with all matrices. The degree of variation was small over the range of HbCO content (~0.5% increase). The matrix method overestimates the amount of total hemoglobin relative to the Cyanomethemoglobin Assay. The cause of the discrepancy is due in part to the amount of HbCO present in the lot used for these experiments. It has been observed that the rate of oxidation of HbCO with K$_3$Fe(CN)$_6$ is slow with respect to HbO$_2$ (Taylor and Miller (1965) Am. J. Clin. Pathol. 43:265), and there may have been a large amount of HbCO in the measured lot. The conditions employed in the Cyanomethemoglobin Assay are not sufficient to oxidized the HbCO to HbMet, and will therefore underestimate the actual total hemoglobin concentration. All evaluated matrices performed roughly equivalently.

4. All but one set of measurements had relative standard deviation (RSD) values below 4%. The average RSD was 6.61%.

HbTotal Content:

From a sample of another fermentation product from a fermentation of *E. coli* strain SGE127 containing the plasmid pSGE1.1E4 was prepared two elevated HbCO samples. The parent and elevated HbCO samples were then diluted 1:2, 1:5, and 1:100 each in formulation buffer. Evelyn-Malloy HbMet analysis was performed on the parent sample. Total hemoglobin concentration and HbCO content were calculated based upon starting materials.

All samples were then measured spectrophotometrically in triplicate. A 0.1 mm pathlength cell was used for the 47.46 and 23.73 g/L samples, a 1 mm pathlength cell for the 9.49 g/L samples and a 1 cm pathlength cell for the 0.47 g/L samples. Several features of the analysis are noteworthy:

1. Recovery of HbTotal is good across the entire window. All matrices appear to work equally well.
2. The recovery of HbCO appears to be acceptable across the evaluated concentration window. As expected, at higher (80%) HbCO concentrations increased dilution results in lower HbCO recovery. This may be due to actual loss of CO to the solution during dilution. The effect of decreased recovery is not apparent at low HbCO content. The best performance is observed with the All Wave/no Hb matrix.
3. The recovery of HbMet is acceptable at total concentration above 10 g/L. Below this level the apparent HbMet content decreases significantly. It is important to note that the absolute OD of the 0.47 g/L sample were intermediate between the 47.46 and 23.73 g/L samples due to the increased pathlength. Therefore the lack of recovery is not due to the inability of the spectrophotometer to discriminate small absorption changes. Excluding the 0.47 g/L samples the best performance was observed with the 6 Wave/Hb matrix.
4. All but two sets of measurements had relative standard deviation (RSD) values below 5%. The average RSD was 3.13%.

One possible explanation for the observed loss of spectrophotometric recovery of rHb1.1 species at low concentration is that there are distinct changes in the extinction coefficient of the rHb1.1 species at different concentrations. Nonlinear optical effects in hemoglobin ligation with oxygen have been reported (Ownby and Gill (1990) Biophys. Chem. 37:395) possibly due to changes in protein conformation during oxygen loading.

Dilution of the samples measured produced the following noteworthy results:

1. In the case of HbTotal, the dilute extinction coefficients gave superior results for the samples at 0.5 and 10 g/L, but overestimated the concentrations at 25 and 50 g/L.
2. In the case of HbCO dilute extinction coefficients did not dramatically affect the average results, but did give more consistent results with respect to the type of matrix.

Based upon the collected data the use of a pseudoinverse matrix solution to determine the concentration of hemoglobin species in rHb1.1 solutions, the All Wave/Hb matrix performed most consistently better than other matrices. The total hemoglobin concentration appears to have an effect on the extinction coefficients of constituent species. At low concentrations (below 10 g/L) a unique matrix must be employed to obtain accurate concentration and composition values.

B. Spectrophotometric Method Using Absorbance Rations

CO saturation can also be measured by use of the ratio of absorbances at 420 and 412 nm (Small (1971) J. Appl. Physiol. 31(1):154–160). The fraction of HbCO present can be calculated using a set of coefficients empirically determined from a total of 21 measurements of the 420/412 ratio at various dilutions, with and without CO sparging of the dilutions. A preferred diluent used is 10 mM sodium borate, pH 10.3 at room temperature. As little as 20 seconds of exposure to CO is required to obtain stable maximal absorbances.

These measurements of 420/412 at zero CO gave a value of 0.872±0.004, After fully saturating with CO (e.g. no change in the ratio upon repeated spargings of the diluted sample with CO), the 420/412 ratio stabilized at 1.490±0.003. The modified Small equation for recombinant hemoglobin becomes:

$$fCO = ([A420/A412] - 0.872)/0.618$$

There was a range of values for the 21 measurements which span a percent CO range of about 2–3%. It is therefore still possible to get an occasional negative number for a given no-CO sample because of the inherent error in the measurements. There is also some indication that for impure samples, there may be some interferences which can skew the ratios slightly. In addition, Met-Hb is known to interfere with the ratio, but only at concentrations above about 10%. Because of sensitivity and interference limitations, this assay is not suitable for high accuracy determinations of CO-Hb, but may be used to assess progress through a given purification run.

Example 6

Method of Measuring Protoporphyrin IX Content in a Crude Protoporphyrin IX-Containing Hemoglobin Solution Protoporphyrin IX levels in the crude hemoglobin solution were measured by a number of methods known to those skilled in the art. Most preferably, the determination of the protoporphyrin IX (PIX) content in hemoglobin samples were accomplished by HPLC (high pressure liquid chromatography) analysis based on the separation of heme and protoporphyrin IX from globin on a reversed phase column. Samples were diluted to approximately 1 mg/ml hemoglobin prior to analysis. To ensure that all heme compounds were quantitated with the same color factor, all heme in the solution was oxidized to hemin before analysis. This was accomplished by mixing $K_3[Fe(CN)_6]$ with the hemoglobin sample just before injection of the sample onto the column to oxidize $Fe^{2+}$ in heme to $Fe^{3+}$. Elution of heme, protoporphyrin IX, and globins was accomplished by an increasingly nonpolar buffer gradient (e.g., water/TFA to acetonitrile). Spectra of hemin and protoporphyrin IX are similar, with absorption maxima at 398 nm and 405 nm, respectively. At 396 nm, color factors for heme and protoporphyrin IX were almost equal, therefore the areas under each peak correspond directly to the relative content of each component. Levels of protoporphyrin IX less than 0.2% (protoporphyrin IX/heme+protoporphyrin IX) were considered to lie below the detection limit of preferred analytical methodologies. Spectral measurements are made anywhere in the range of about 390–410 nm with similar results.

The foregoing written specification is considered to be sufficient to enable one skilled in the art to practice the invention. The deposit of materials herein does not constitute an admission that the written description herein contained is inadequate to enable the practice of any aspect of the invention, including the best mode thereof, nor is this deposit to be construed as limiting the scope of the claims to the specific illustrations which materials deposited represent.

We claim:

1. A method for the production of a substantially protoporphyrin IX free hemoglobin solution comprising: heating a crude protoporphyrin IX-containing hemoglobin solution for a sufficient time of less than 5 minutes and at a sufficient temperature to reduce protoporphyrin IX-containing hemoglobin to insignificant levels to produce the substantially protoporphyrin IX free hemoglobin solution.

2. A method for the production of a substantially protoporphyrin IX free hemoglobin solution according to claim 1 wherein the crude protoporphyrin IX-containing hemoglobin solution is a cell lysate of recombinantly produced hemoglobin.

3. A method for the production of a substantially protoporphyrin IX free hemoglobin solution according to claim 1 wherein said insignificant levels of protoporphyrin IX-containing hemoglobin are less than about 6 percent of total hemoglobin.

4. A method for the production of a substantially protoporphyrin IX free hemoglobin solution according to claim 3 wherein said insignificant levels of protoporphyrin IX-containing hemoglobin are less than about 1 percent of total hemoglobin.

5. A method for the production of a substantially protoporphyrin IX free hemoglobin solution according to claim 1 wherein said sufficient temperature is from about 75° C. to about 90° C.

6. A method for the production of a substantially protoporphyrin IX free hemoglobin solution according to claim 5 whereto said sufficient temperature is from about 80° C. to about 85° C.

7. A method for the production of a substantially protoporphyrin IX free hemoglobin solution according to claim 6 wherein said sufficient temperature is about 81° C.

8. A method for the production of a substantially protoporphyrin IX free hemoglobin solution according to claim 1 whereto said sufficient time is less than about 30 seconds.

9. A method for the production of a substantially protoporphyrin IX free hemoglobin solution according to claim 5 wherein said sufficient time is less than about 30 seconds.

10. A method for the production of a substantially protoporphyrin IX free hemoglobin solution according to claim 6 wherein said sufficient time is less than about 30 seconds.

11. A method for the production of a substantially protoporphyrin IX free hemoglobin solution according to claim 7 whereto said sufficient time is less than about 30 seconds.

12. A method for the production of a substantially protoporphyrin IX free hemoglobin solution according to claim 8 wherein said sufficient time is from about 5 to about 15 seconds.

13. A method for the production of a substantially protoporphyrin IX free hemoglobin solution according to claim 9 wherein said sufficient time is from about 5 to about 15 seconds.

14. A method for the production of a substantially protoporphyrin IX free hemoglobin solution according to claim 10 wherein said sufficient time is from about 5 to about 15 seconds.

15. A method for the production of a substantially protoporphyrin IX free hemoglobin solution according to claim 11 wherein said sufficient time is from about 5 to about 15 seconds.

16. A method for the production of a substantially protoporphyrin IX free hemoglobin solution according to claim 15 wherein said sufficient time is from about 10 to about 11 seconds.

17. The method for the production of a substantially protoporphyrin IX free hemoglobin solution of claim 1, further comprising:

exposing the crude protoporphyrin IX-containing hemoglobin solution to a non-oxygen gas prior to heating.

18. The method of claim 1, wherein said crude protoporphyrin IX-containing hemoglobin solution is deoxygenated prior to heating.

19. A method for the production of a substantially protoporphyrin IX free hemoglobin solution comprising:

(a) exposing a crude protoporphyrin IX-containing hemoglobin solution to a non-oxygen gas, wherein said non-oxygen gas is selected from the group consisting of carbon monoxide and nitric oxide; and (b) heating the crude protoporphyrin IX-containing hemoglobin solution for a sufficient time of less than 5 minutes and at a sufficient temperature to reduce protoporphyrin IX-containing hemoglobin to insignificant levels to produce the substantially protoporphyrin IX free hemoglobin solution.

20. A method for the production of a substantially protoporphyrin IX free hemoglobin solution according to claim 19 wherein said non-oxygen gas is carbon monoxide.

21. A method for the production of a substantially protoporphyrin IX free hemoglobin solution according to claim 20 wherein said non-oxygen gas is essentially pure carbon monoxide.

22. A method for the production of a substantially protoporphyrin IX free hemoglobin solution according to claim 19 wherein said exposure to a non-oxygen gas is via sparging a crude protoporphyrin IX-containing hemoglobin solution after breakage of cells containing protoporphyrin IX-containing hemoglobin.

23. A method for the production of a substantially protoporphyrin IX free hemoglobin solution according to claim 22 wherein said protoporphyrin IX-containing hemoglobin is recombinant hemoglobin.

24. A method for the production of a substantially protoporphyrin IX free hemoglobin solution according to claim 19 wherein said insignificant levels of protoporphyrin IX-containing hemoglobin are less than about 6 percent of total hemoglobin.

25. A method for the production of a substantially protoporphyrin IX free hemoglobin solution according to claim 24 wherein said insignificant levels of protoporphyrin IX-containing hemoglobin are less than about 1 percent of total hemoglobin.

26. A method for the production of a substantially protoporphyrin IX free hemoglobin solution according to claim 19 wherein said sufficient temperature is from about 75° C. to about 90° C.

27. A method for the production of a substantially protoporphyrin IX free hemoglobin solution according to claim 26 wherein said sufficient temperature is from about 80° C. to about 85° C.

28. A method for the production of a substantially protoporphyrin IX free hemoglobin solution according to claim 27 wherein said sufficient temperature is about 81° C.

29. A method for the production of a substantially protoporphyrin IX free hemoglobin solution according to claim 19 wherein said sufficient time is less than about 30 seconds.

30. A method for the production of a substantially protoporphyrin IX free hemoglobin solution according to claim 26 wherein said sufficient time is less than about 30 seconds.

31. A method for the production of a substantially protoporphyrin IX free hemoglobin solution according to claim 27 wherein said sufficient time is less than about 30 seconds.

32. A method for the production of a substantially protoporphyrin IX free hemoglobin solution according to claim 28 wherein said sufficient time is less than about 30 seconds.

33. A method for the production of a substantially protoporphyrin IX free hemoglobin solution according to claim 29 wherein said sufficient time is from about 5 to about 15 seconds.

34. A method for the production of a substantially protoporphyrin IX free hemoglobin solution according to claim 30 wherein said sufficient time is from about 5 to about 15 seconds.

35. A method for the production of a substantially protoporphyrin IX free hemoglobin solution according to claim 31 wherein said sufficient time is from about 5 to about 15 seconds.

36. A method for the production of a substantially protoporphyrin IX free hemoglobin solution according to claim 32 wherein said sufficient time is from about 5 to about 15 seconds.

37. A method for the production of a substantially protoporphyrin IX free hemoglobin solution according to claim 36 wherein said sufficient time is from about 10 to about 11 seconds.

38. A method for the production of a substantially protoporphyrin IX free hemoglobin solution comprising:

(a) exposing, via sparging, a crude protoporphyrin IX-containing hemoglobin solution to essentially pure carbon monoxide after breakage of cells containing a recombinant protoporphyrin IX-containing hemoglobin followed by (b) heating the crude protoporphyrin IX-containing hemoglobin solution via steam injection for from about 10 to about 11 seconds at about 81° C. to reduce protoporphyrin IX-containing hemoglobin in said crude protoporphyrin IX-containing hemoglobin solution to less than about 1 percent of total hemoglobin, wherein said steam injection is accomplished with expansion steam injection.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 45
( B ) TYPE: nucleic acid
( C ) STRANDEDNESS: single
( D ) TOPOLOGY: linear ( i i ) MOLECULE TYPE: C-term of a gene,Xba I site ( i i i ) HYPOTHETICAL: no ( x i ) SEQUENCE DESCRIPTION: SEQ ID NO:1:

CGGGAATACG GTCTAGATCA TTAACGGTAT TTCGAAGTCA GAACG      45

( 2 ) INFORMATION FOR SEQ ID NO:2:

( i ) SEQUENCE CHARACTERISTICS:
( A ) LENGTH: 95
( B ) TYPE: nucleic acid
( C ) STRANDEDNESS: single
( D ) TOPOLOGY: linear ( i i ) MOLECULE TYPE: tac promoter sequence, Bam HI-Eag I sites ( i i i ) HYPOTHETICAL: no ( x i ) SEQUENCE DESCRIPTION: SEQ ID NO:2:

GATCCGAGCT GTTGACAATT AATCATCGGC TCGTATAATG TGTGGAATTG      50

TGACGGATAA CAATTTCACA CAGGAAATTA ATTAATGCTG TCTCC            95

( 2 ) INFORMATION FOR SEQ ID NO:3:

( i ) SEQUENCE CHARACTERISTICS:
( A ) LENGTH: 96
( B ) TYPE: nucleic acid
( C ) STRANDEDNESS: single
( D ) TOPOLOGY: linear ( i i ) MOLECULE TYPE: tac promoter, Bam HI - Eag I sites ( i i i ) HYPOTHETICAL: no ( x i ) SEQUENCE DESCRIPTION: SEQ ID NO:3:

GGCCGGAGAC AGCATTAATT AATTTCCTGT GTGAAATTGT TATCCGCTCA      50

CAATTCCACA CATTATACGA GCCGATGATT AATTGTCAAC AGCTCG            96

( 2 ) INFORMATION FOR SEQ ID NO:4:

( i ) SEQUENCE CHARACTERISTICS:
( A ) LENGTH: 64
( B ) TYPE: nucleic acid
( C ) STRANDEDNESS: single
( D ) TOPOLOGY: linear ( i i ) MOLECULE TYPE: 5'end of alpha gene,with EcoR1, BamH1 and Eag1 sites ( i i i ) HYPOTHETICAL: no ( x i ) SEQUENCE DESCRIPTION: SEQ ID NO:4:

TCGGATTCGA ATTCCAAGCT GTTGGATCCT TAGATTGAAC TGTCTCCGGC     50

CGATAAAACC ACCG     64

( 2 ) INFORMATION FOR SEQ ID NO:5:

( i ) SEQUENCE CHARACTERISTICS:
        ( A ) LENGTH: 55
        ( B ) TYPE: nucleic acid
        ( C ) STRANDEDNESS: single
        ( D ) TOPOLOGY: linear ( i i ) MOLECULE TYPE: 5'end of beta with Xba I site ( i i i ) HYPOTHETICAL: no ( x i ) SEQUENCE DESCRIPTION: SEQ ID NO:5:

CGGAAGCCCA ATCTAGAGGA AATAATATAT GCACCTGACT CCGGAAGAAA     50

AATCC     55

( 2 ) INFORMATION FOR SEQ ID NO:6:

( i ) SEQUENCE CHARACTERISTICS:
        ( A ) LENGTH: 44
        ( B ) TYPE: nucleic acid
        ( C ) STRANDEDNESS: single
        ( D ) TOPOLOGY: linear ( i i ) MOLECULE TYPE: 3'end of the beta gene with Hind III
        site ( i i i ) HYPOTHETICAL: no ( x i ) SEQUENCE DESCRIPTION: SEQ ID NO:6:

CCCGAAACCA AGCTTCATTA GTGAGCTAGC GCGTTAGCAA CACC     44

( 2 ) INFORMATION FOR SEQ ID NO:7:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:7:

TTTAAGCTTC ATTAGTGGTA TTTGTGAGCT AGCGCGT     37

( 2 ) INFORMATION FOR SEQ ID NO:8:

( i ) SEQUENCE CHARACTERISTICS:
        ( A ) LENGTH: 37
        ( B ) TYPE: nucleic acid
        ( C ) STRANDEDNESS: single
        ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:8:

CAGCATTAAT TAACCTCCTT AGTGAAATTG TTATCCG     37

( 2 ) INFORMATION FOR SEQ ID NO:9:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( i i ) MOLECULE TYPE: mutagenesis reverse primer ( i i i ) HYPOTHETICAL: no ( x i ) SEQUENCE DESCRIPTION: SEQ ID NO:9:

```
GGTGCATATA TTTACCTCCT TATCTAGATC ATTAACGGTA TTTCG                45
```

( 2 ) INFORMATION FOR SEQ ID NO:10:

( i ) SEQUENCE CHARACTERISTICS:
        ( A ) LENGTH: 10
        ( B ) TYPE: nucleic acid
        ( C ) STRANDEDNESS: single
        ( D ) TOPOLOGY: linear ( i i ) MOLECULE TYPE: Pme I linker ( i i i ) HYPOTHETICAL: no ( x i ) SEQUENCE DESCRIPTION: SEQ ID NO:10:

```
GGTTTAAACC                                                       10
```

( 2 ) INFORMATION FOR SEQ ID NO:11:

( i ) SEQUENCE CHARACTERISTICS:
        ( A ) LENGTH: 58
        ( B ) TYPE: nucleic acid
        ( C ) STRANDEDNESS: single
        ( D ) TOPOLOGY: linear ( i i ) MOLECULE TYPE: oligonucleotide upstream of lacI gene ( i i i ) HYPOTHETICAL: no ( x i ) SEQUENCE DESCRIPTION: SEQ ID NO:11:

```
GGCGAATAAA AGCTTGCGGC CGCGTTGACA CCATCGAATG GCGCAAAACC           50
TTTCGCGG                                                         58
```

( 2 ) INFORMATION FOR SEQ ID NO:12:

( i ) SEQUENCE CHARACTERISTICS:
        ( A ) LENGTH: 69
        ( B ) TYPE: nucleic acid
        ( C ) STRANDEDNESS: single
        ( D ) TOPOLOGY: linear ( i i ) MOLECULE TYPE: downstream side of lacI gene ( i i i ) HYPOTHETICAL: no ( x i ) SEQUENCE DESCRIPTION: SEQ ID NO:12:

```
GGGCAAATAG GATCCAAAAA AAAGCCCGCT CATTAGGCGG GCTTTATCAC            50
TGCCCGCTTT CCAGTCGGG                                              69
```

( 2 ) INFORMATION FOR SEQ ID NO:13:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( i i ) MOLECULE TYPE: primer for pBR322 ori positions
3170- 3148

( i i i ) HYPOTHETICAL: no ( x i ) SEQUENCE DESCRIPTION: SEQ ID NO:13:

CCCCGAAAAG GATCCAAGTA GCCGGCGGCC GCGTTCCACT GAGCGTCAGA      50

CCCC      54

( 2 ) INFORMATION FOR SEQ ID NO:14:

( i ) SEQUENCE CHARACTERISTICS:
( A ) LENGTH: 42
( B ) TYPE: nucleic acid
( C ) STRANDEDNESS: single
( D ) TOPOLOGY: linear ( i i ) MOLECULE TYPE: primer for pBR322 ori positions
2380- 2404

( i i i ) HYPOTHETICAL: no ( x i ) SEQUENCE DESCRIPTION: SEQ ID NO:14:

GGCGGTCCTG TTTAAACGCT GCGCTCGGTC GTTCGGCTGC GG      42

( 2 ) INFORMATION FOR SEQ ID NO:15:

( i ) SEQUENCE CHARACTERISTICS:
( A ) LENGTH: 28
( B ) TYPE: nucleic acid
( C ) STRANDEDNESS: single
( D ) TOPOLOGY: linear ( i i ) MOLECULE TYPE: dialpha gene fragment ( i i i ) HYPOTHETICAL: no ( x i ) SEQUENCE DESCRIPTION: SEQ ID NO:15:

CAATTTCACA GGAAATTAAT TAATGCTG      28

( 2 ) INFORMATION FOR SEQ ID NO:16:

( i ) SEQUENCE CHARACTERISTICS:
( A ) LENGTH: 30
( B ) TYPE: nucleic acid
( C ) STRANDEDNESS: single
( D ) TOPOLOGY: linear ( i i ) MOLECULE TYPE: dialpha gene fragment ( i i i ) HYPOTHETICAL: no ( x i ) SEQUENCE DESCRIPTION: SEQ ID NO:16:

CAATTTCACT AAGGAGGTTA ATTAATGCTG      30

( 2 ) INFORMATION FOR SEQ ID NO:17:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) MOLECULE TYPE: beta gene fragment ( i i i ) HYPOTHETICAL: no ( x i ) SEQUENCE DESCRIPTION: SEQ ID NO:17:

TAAAGATCTA GAGGAAATAA TATATGCAC      29

( 2 ) INFORMATION FOR SEQ ID NO:18:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) MOLECULE TYPE: beta gene fragment ( i i i ) HYPOTHETICAL: no ( x i ) SEQUENCE DESCRIPTION: SEQ ID NO:18:

TAATGATCTA GATAAGGAGG TAAATATATG CAC    33

( 2 ) INFORMATION FOR SEQ ID NO:19:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) MOLECULE TYPE: beta terminus ( i i i ) HYPOTHETICAL: no ( x i ) SEQUENCE DESCRIPTION: SEQ ID NO:19:

CTCGCTCACT AATGAA    16

( 2 ) INFORMATION FOR SEQ ID NO:20:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) MOLECULE TYPE: modified beta terminus ( i i i ) HYPOTHETICAL: no ( x i ) SEQUENCE DESCRIPTION: SEQ ID NO:20:

CTCGCTCACA AATACCACTA ATGAA    25